(12) United States Patent
Doyle et al.

(10) Patent No.: US 11,938,258 B2
(45) Date of Patent: Mar. 26, 2024

(54) EXTRACORPOREAL DEVICE AND METHOD FOR REMOVAL OF SECONDARY MEMBRANE

(71) Applicant: Fresenius Medical Care Holdings, Inc., Waltham, MA (US)

(72) Inventors: Matthew Doyle, Martinez, CA (US); Robert Anthony Zimmerman, Millbrae, CA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 0 days.

(21) Appl. No.: 17/705,574

(22) Filed: Mar. 28, 2022

(65) Prior Publication Data

US 2022/0370699 A1 Nov. 24, 2022

Related U.S. Application Data

(60) Provisional application No. 63/188,624, filed on May 14, 2021.

(51) Int. Cl.
*A61M 1/34* (2006.01)
*A61M 1/36* (2006.01)

(52) U.S. Cl.
CPC ........ *A61M 1/3479* (2014.02); *A61M 1/3403* (2014.02); *A61M 1/3441* (2013.01); *A61M 1/365* (2014.02)

(58) Field of Classification Search
None
See application file for complete search history.

(56) References Cited

U.S. PATENT DOCUMENTS 5,580,460 A * 12/1996 Polaschegg ......... A61M 1/1617
210/138
6,423,231 B1 * 7/2002 Collins ............... A61M 1/3434
604/4.01

(Continued)

FOREIGN PATENT DOCUMENTS

DE 102016107024 A1 10/2017
KR 1020070009642 A 1/2007
WO 2011082783 A1 7/2011

OTHER PUBLICATIONS

International Search Report for PCT Application No. PCT/US2022/022141, dated Jul. 25, 2022 (6 Pages).

(Continued)

*Primary Examiner* — Krishnan S Menon
(74) *Attorney, Agent, or Firm* — Kilyk & Bowersox, P.L.L.C.

(57) ABSTRACT

An extracorporeal blood treatment device and a method are provided for removing a secondary membrane formed on a semipermeable membrane of a dialyzer during an extracorporeal blood treatment. The extracorporeal blood treatment device operates in a first operating mode in which a dialysate outlet valve is open such that dialysate flows through a dialyzer feed line, through a dialysate chamber, and into and through a dialyzer discharge line. The extracorporeal blood treatment device operates in a second operating mode to remove the secondary membrane from the semipermeable membrane. During the second operating mode, the dialysate outlet valve is closed for a duration of time such that dialysate is prevented from flowing through the dialyzer discharge line. A backflush procedure results wherein a volume of dialysate passes from the dialysate chamber through the semipermeable membrane and into the blood chamber.

15 Claims, 8 Drawing Sheets

(56) References Cited

U.S. PATENT DOCUMENTS

| | | |
|---|---|---|
| 7,500,958 B2 | 3/2009 | Asbrink et al. |
| 9,173,986 B2 | 11/2015 | Heide et al. |
| 10,940,254 B2 | 3/2021 | Hacker |
| 2005/0230314 A1* | 10/2005 | Kim .................... A61M 1/3607 |
| | | 210/646 |
| 2005/0251086 A1 | 11/2005 | Sternby |
| 2012/0267309 A1 | 10/2012 | Peters et al. |
| 2012/0273415 A1* | 11/2012 | Gerber .................. B01D 61/00 |
| | | 210/741 |
| 2015/0238680 A1 | 8/2015 | Kelly et al. |
| 2016/0310655 A1 | 10/2016 | Wiktor et al. |
| 2017/0296726 A1 | 10/2017 | Reimenschneider |
| 2020/0155745 A1 | 5/2020 | Nilsson et al. |

OTHER PUBLICATIONS

Written Opinion of International Searching Authority, for PCT/US2022/022141, dated Jul. 25, 2022 (3 Pages).

Rockel et al., Permeability and secondary membrane formation of a high flux polysulfone hemofilter, Kidney International, vol. 30, (1986), pp. 429-432.

* cited by examiner

Coefficients for Device Setting Variables

| Device Setting Variable | Discrete Modifier (minutes) | % Modifier | Coefficient of Modification (Only for % modifiers) |
|---|---|---|---|
| Substitution Fluid Rate (< 75 ml/min) | N/A | 0 | $Q_s = Q_{s\text{-normal}} (Q_{sn}) = 1$ |
| Substitution Fluid Rate (75-150 ml/min) | N/A | $Q_s$ modifier = -2% | $Q_s = Q_{sn} = 0.98$ |
| Substitution Fluid Rate (150-225 ml/min) | N/A | $Q_s$ modifier = -4% | $Q_s = Q_{sn} = 0.96$ |
| Substitution Fluid Rate (225-300 ml/min) | N/A | $Q_s$ modifier = -6% | $Q_s = Q_{sn} = 0.94$ |
| Substitution Fluid Rate (300-375 ml/min) | N/A | $Q_s$ modifier = -8% | $Q_s = Q_{sn} = 0.92$ |
| Substitution Fluid Rate (> 375 ml/min) | N/A | $Q_s$ modifier = -10% | $Q_s = Q_{sn} = 0.9$ |
| UF Rate (0-500 ml/hr) | N/A | 0 | $Q_{uf} = 1$ |
| UF Rate (500-1000 ml/hr) | N/A | -3% | $Q_{uf} = 0.97$ |
| UF Rate (1000-1500 ml/hr) | N/A | -6% | $Q_{uf} = 0.94$ |
| UF Rate (1500-2000 ml/hr) | N/A | -8% | $Q_{uf} = 0.92$ |
| UF Rate (2000-2500 ml/hr) | N/A | -10% | $Q_{uf} = 0.9$ |
| UF Rate (2500-3000 ml/hr) | N/A | -12% | $Q_{uf} = 0.88$ |
| UF Rate (3000-3500 ml/hr) | N/A | -14% | $Q_{uf} = 0.86$ |
| UF Rate (>3500ml/hr) | N/A | -15% | $Q_{uf} = 0.85$ |
| Blood Flow Rate (0-150 ml/min) | N/A | 0 | $Q_b = 1$ |
| Blood Flow Rate (150-300 ml/min) | N/A | -3% | $Q_b = 0.97$ |
| Blood Flow Rate (300-450 ml/min) | N/A | -6% | $Q_b = 0.94$ |
| Blood Flow Rate (450-600 ml/min) | N/A | -9% | $Q_b = 0.91$ |
| Optiflux 160 NR | 0 | 0 | $X_d = 1$ |
| Optiflux 180 NR | -3 | -5% | $X_d = 0.95$ |
| Optiflux 200 NR | -2.5 | -4.5% | $X_d = 0.955$ |
| Optiflux 250 NR | -4 | -10% | $X_d = 0.9$ |
| Dialyzer (Custom) - Ultrafiltration Coefficient < 55 [ml/hr/mmHg] @ 300 Qd | 0 | 0% | $X_d = 1$ |
| Dialyzer (Custom) - Ultrafiltration Coefficient 55-100 [ml/hr/mmHg] @ 300 Qd | -2.5 | -4.5% | $X_d = 0.955$ |
| Dialyzer (Custom) - Ultrafiltration Coefficient > 100 [ml/hr/mmHg] @ 300 Qd | -4 | -10% | $X_d = 0.9$ |

FIG. 2A

Coefficients for Device Setting Variables

| Device Setting Variable | Discrete Modifier (minutes) | % Modifier | Coefficient of Modification (Only for % modifiers) |
|---|---|---|---|
| HDF treatment (predilution) | N/A | Multiply $Q_s$ modifier by -1 | $Q_s = Q_{s\text{-modified}} (Q_{sm}) = 2 - Q_{sn}$ |
| HF treatment (predilution) | N/A | Multiply $Q_s$ modifier by -1 | $Q_s = Q_{s\text{-modified}} (Q_{sm}) = 2 - Q_{sn}$ |
| HDF treatment (postdilution) | N/A | Multiply $Q_s$ modifier by 1 | $Q_{sn}$ |
| HF treatment (postdilution) | N/A | Multiply $Q_s$ modifier by 1 | $Q_{sn}$ |
| Substitution Fluid Bolus (postdilution) (< 100 ml) | -5 | -10% | $V_B = 0.9$ |
| Substitution Fluid Bolus (postdilution) (> 100 ml) | -12 | -25% | $V_B = 0.75$ |
| Substitution Fluid Bolus (predilution) (< 100 ml) | +5 | 10% | $V_B = 1.1$ |
| Substitution Fluid Bolus (predilution) (> 100 ml) | +12 | 25% | $V_B = 1.25$ |
| ΔUF Rate > 500 ml/hr | -4 | -10% | $\Delta Q_{ufcm} = 0.9$ |
| ΔUF Rate > 1500 ml/hr | -4 | -10% | $\Delta Q_{ufcm} = 0.9$ |
| ΔBlood Flow Rate > 100 ml/min | -4 | -10% | $\Delta Q_{bcm} = 0.9$ |
| ΔSubstitution Fluid Rate > 100 ml/min | -4 | -10% | $\Delta Q_{scm} = 0.9$ |

FIG. 2B

Coefficients for Device Output Variables

| Device Output Variable | Discrete Modifier (minutes) | % Modifier | Coefficient of Modification (Only for % modifiers) |
|---|---|---|---|
| Run Number (First Run) | N/A | -40% | $R_n = 0.6$ |
| Run Number (Second and Subsequent Runs) | N/A | 0 | $R_n = 1$ |
| Venous Pressure (0-200 mmHg) | N/A | 0% | $P_V = 1$ |
| Venous Pressure (200-300 mmHg) | N/A | -4% | $P_V = 0.96$ |
| Venous Pressure (300-400 mmHg) | N/A | -8% | $P_V = 0.92$ |
| Transmembrane Pressure (0-75 mmHg) | N/A | 0 | $P_{TM} = 1$ |
| Transmembrane Pressure (75-150 mmHg) | N/A | -2% | $P_{TM} = 0.98$ |
| Transmembrane Pressure (150-225 mmHg) | N/A | -4% | $P_{TM} = 0.96$ |
| Transmembrane Pressure (225-300 mmHg) | N/A | -6% | $P_{TM} = 0.94$ |
| Transmembrane Pressure > 300 mmHg | N/A | -8% | $P_{TM} = 0.92$ |
| ΔUF coefficient > 15% (decrease) | -4 | -10% | $\Delta UFC_{cm} = 0.9$ |
| ΔUF coefficient > 25% (decrease) | -8 | -20% | $\Delta UFC_{cm} = 0.8$ |
| ΔHct > 15% (increase) | -4 | -10% | $\Delta Hct_{cm} = 0.9$ |
| ΔTMP = 5% (increase) (Reset if Qd, Qs, Qb, changed. Cumulative for multiple increases) | -4 | -10% | $\Delta TMP_{cm} = 0.9$ (commensurate with ΔTMP) |
| ΔTMP = 10% (increase) (Reset if Qd, Qs, Qb, changed. Cumulative for multiple increases) | -8 | -20% | $\Delta TMP_{cm} = 0.8$ (commensurate with ΔTMP) |
| ΔTMP = 15% (increase) (Reset if Qd, Qs, Qb, changed. Cumulative for multiple increases) | -12 | -30% | $\Delta TMP_{cm} = 0.7$ (commensurate with ΔTMP) |
| ΔK > 15% (decrease) | -4 | -10% | $\Delta Clearance_{cm} = \Delta K_{cm} = 0.9$ |

FIG. 3

EXTRACORPOREAL DEVICE AND METHOD FOR REMOVAL OF SECONDARY MEMBRANE

CROSS-REFERENCE TO RELATED APPLICATION

The present application claims priority from U.S. Provisional Patent Application No. 63/188,624 filed May 14, 2021, which is incorporated herein by reference in its entirety.

FIELD OF THE INVENTION

The present invention relates to devices and methods for the treatment of blood extracorporeally, such as by hemodialysis, hemofiltration, and hemodiafiltration.

BACKGROUND OF THE INVENTION

Renal replacement therapy systems are used for patients that have to treat their blood outside of their bodies. An extracorporeal blood treatment can be used to extract undesirable substances or molecules from the patient's blood, and, if necessary, to add desirable substances or molecules to the blood. The extracorporeal blood treatment is accomplished by passing blood through a dialyzer. A semipermeable membrane separates the dialyzer into a blood chamber and a dialysate chamber. Blood withdrawn from the patient is introduced into the blood chamber and flows past the semipermeable membrane. The semipermeable membrane selectively allows matter in the blood to flow across the semipermeable membrane from the blood chamber into the dialysate chamber. The semipermeable membrane also selectively allows matter in the dialysate chamber to flow across the semipermeable membrane into the blood chamber, depending on the type of treatment.

A number of different types of extracorporeal blood treatments can be performed. In a hemofiltration (HF) treatment, blood flows past the semipermeable membrane and undesirable matter and toxins from the blood are pulled across the semipermeable membrane and carried away by dialysate. Meanwhile, desirable matter is added to the blood, typically by dispensing dialysate or a substituate, also known as a substitution fluid, into the blood either before or after the blood passes through the dialyzer, and before the blood is returned to the patient. In a hemodialysis (HD) treatment, dialysate containing desirable matter is introduced into the dialysate chamber of the dialyzer. Undesirable matter from the blood crosses the semipermeable membrane into the dialysate and desirable matter from the dialysate can cross the semipermeable membrane into the blood. In a hemodiafiltration (HDF) treatment, blood and dialysate exchange matter as in HD, and, in addition, matter is added to the blood, typically by dispensing dialysate into the treated blood before its return to the patient as in HF. Ultrafiltration (UF) includes the removal of undesirable matter from the blood by convection across the semipermeable membrane into the dialysate chamber.

Coagulation of the blood, also referred to as clotting, is usually reduced by using anti-coagulants, such as heparin. However, during treatment, material from the blood such as clotted blood, pathogenic cytokines, chemokines, myocardial depressant factors, C' activating proteins, and the like, can clog the semipermeable membrane of the dialyzer. This phenomenon can be referred to as membrane fouling or secondary membrane formation. The effects on the semipermeable membrane are a progressive decline in flux and a change of semipermeable membrane selectivity. Membrane fouling is mainly caused by concentration polarization and protein adsorption or deposition on the surface of the semipermeable membrane or in its pores. Concentration polarization is a result of a concentration gradient due to solute accumulation near the semipermeable membrane surface. This solute accumulation is also referred to as a secondary membrane. Protein adsorption or deposition on the surface or in its pores is caused by proteins that are adsorbed or trapped in the pores of the semipermeable membrane, and thereby changes the semipermeable membrane properties. When regions of the semipermeable membrane start to become less effective, action has to be taken to maintain the same efficiency of the treatment.

Secondary membranes have been previously managed by rinsing the blood circuit and changing the filter. However, these procedures are time consuming and the treatment has to be stopped. Other devices and methods for removing secondary membranes during treatment require the use of additional sets of dialysate lines, sensors, pumps, and the like, that are unnecessarily complicated and require expensive modifications to extracorporeal blood treatment devices.

Accordingly, a need exists for a device and method for removing a secondary membrane formed during an extracorporeal blood treatment, which are efficient and enable inexpensive modifications of existing extracorporeal blood treatment devices.

SUMMARY OF THE PRESENT INVENTION

A feature of the present invention is to provide an extracorporeal device and method that removes secondary membrane from a semipermeable membrane of a dialyzer.

Another feature of the present invention to provide an extracorporeal device and method that removes secondary membrane from a semipermeable membrane of a dialyzer during an extracorporeal treatment of a patient.

A further feature of the present invention is to provide an extracorporeal device that intermittently removes secondary membrane from a semipermeable membrane of a dialyzer during an extracorporeal treatment of a patient.

Still a further feature of the present invention is to provide modifications to an extracorporeal device to intermittently remove secondary membrane from a semipermeable membrane of a dialyzer during an extracorporeal treatment of a patient.

An additional feature of the present invention is to provide an extracorporeal device that intermittently introduces a controlled volume of dialysate from a dialysate chamber through a semipermeable membrane to a blood chamber of a dialyzer, to remove secondary membrane from the semipermeable membrane during an extracorporeal treatment of a patient.

A further feature of the present invention is to provide an extracorporeal device that detects a build-up of secondary membrane on a semi-permeable membrane of a dialyzer and removes the secondary membrane from a semipermeable membrane during extracorporeal treatment of a patient upon detection of the build-up.

Yet a further feature of the present invention is to provide a processor for an extracorporeal device, which is programmed or otherwise configured to carry out a set of instructions to remove secondary membrane from a semipermeable membrane during an extracorporeal treatment of a patient Yet a further feature of the present invention is to provide a processor for an extracorporeal device, which is programmed or otherwise configured to carry out a set of instructions to detect a build-up of secondary membrane on a semi-permeable membrane of a dialyzer, and to remove the secondary membrane from the semipermeable membrane, upon detection of the build-up, during an extracorporeal treatment of a patient.

Additional features and advantages of the present invention will be set-forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to an extracorporeal blood treatment device. The extracorporeal blood treatment device includes a dialyzer having a blood chamber, a dialysate chamber, a dialysate inlet, a dialysate outlet, and a semipermeable membrane. The blood chamber and the dialysate chamber are divided from one another by the semipermeable membrane. A dialyzer feed line leads to the dialysate inlet and is configured to supply dialysate to the dialysate chamber. A dialyzer discharge line leads away from the dialysate outlet and is configured to carry dialysate away from the dialysate chamber. A dialysate pump is configured to pump dialysate through the dialyzer feed line to the dialysate chamber and from the dialysate chamber out through the dialyzer discharge line.

A flow pump, for example, downstream of a return line, and/or an ultrafiltrate pump, can be configured to be switched between an operating state and a non-operating state. In the operating state, the ultrafiltrate pump pulls liquid from the blood chamber, through the semipermeable membrane, into the dialysate chamber, and away from the dialysate chamber.

The dialysate pump is configured to operate in a first operating mode of the extracorporeal blood treatment device and a second operating mode of the extracorporeal blood treatment device. The first operating mode operates in a configuration where a dialysate outlet valve is open such that dialysate flows through the dialyzer feed line, through the dialysate chamber, and into and through the dialyzer discharge line. The second operating mode operates in a configuration where the dialysate outlet valve is closed for a duration of time, the ultrafiltrate pump is switched to the non-operating state, dialysate is prevented from flowing through the dialyzer discharge line, and a volume of dialysate passes from the dialysate chamber through the semipermeable membrane and into the blood chamber. A balancing chamber can be equipped such that the valve is closed and then reopened to allow the balancing chamber cycle to finish.

The present invention further relates to the extracorporeal blood treatment device having a processor and a sensor or sensor system in communication with the processor. The sensor or sensor system is configured to generate sensor data and the processor is configured to process the sensor data. The processor is further configured to switch the extracorporeal blood treatment device to the second operating mode, from the first operating mode, for a period of time, based on the sensor data processed.

The present invention further relates to the processor being configured to determine, based on the sensor data, that a secondary membrane is building up on the semipermeable membrane. The processor hastens the switching of the extracorporeal blood treatment device to the second operating mode from the first operating mode, for the period of time, when the processor determines that the secondary membrane is building up on the semipermeable membrane The present invention also relates to a method of blood treatment that includes utilizing the extracorporeal blood treatment device of the present invention for blood treatment of a patient and intermittently removing secondary membrane from the semipermeable membrane during blood treatment.

The present invention also relates to a processor for an extracorporeal device, which is programmed or otherwise configured to carry out a set of instructions to remove secondary membrane from a semipermeable membrane during an extracorporeal treatment of a patient.

The present invention also relates to a processor for an extracorporeal device, which is programmed or otherwise configured to carry out a set of instructions to detect a build-up of secondary membrane on a semi-permeable membrane of a dialyzer, and to remove the secondary membrane from the semipermeable membrane, upon detection of the build-up, during an extracorporeal treatment of a patient.

The present invention, in addition, relates to a method of blood treatment. The method includes: a) providing an extracorporeal blood treatment device including a dialyzer having a blood chamber, a dialysate chamber, and a semipermeable membrane, the blood chamber and the dialysate chamber being divided from one another by the semipermeable membrane, the dialysate chamber having a dialysate outlet valve; b) treating blood in a first operating mode by pumping dialysate through the dialysate chamber with a dialysate pump, pumping the blood through the blood chamber with a blood pump, and pulling ultrafiltrate out of the dialysate chamber with an ultrafiltrate pump; c) detecting a build-up of a secondary membrane on the semipermeable membrane while treating the blood in the first operating mode; and d) switching from the first operating mode to a second operating mode upon detecting of the build-up, the second operating mode includes closing the dialysate outlet valve for a duration of time and shutting off the ultrafiltrate pump to prevent dialysate from flowing out of the dialysate chamber so that a volume of dialysate passes from the dialysate chamber to the blood chamber through the semipermeable membrane. Ultrafiltration need not be related to preventing flow, but can be controlled to ensure an accurate ultrafiltration volume calculation.

It is to be understood that both the foregoing general description and the following detailed description are exemplary and explanatory only and are intended to provide a further explanation of the present invention, as claimed.

BRIEF DESCRIPTION OF THE DRAWINGS

The drawings represent various design features of the present invention. Similar referencing identifiers in different figures can refer to similar features unless indicated otherwise. The drawings are not necessarily to scale.

FIG. 2A is a table of device setting variables and corresponding coefficients of modification for modifying a base time and generating a time interval.

FIG. 2B is a table of device setting variables and corresponding coefficients of modification for modifying a base time and generating a time interval.

FIG. 3 is a table of device output variables and corresponding coefficients of modification for modifying a base time and generating a time interval.

DETAILED DESCRIPTION OF THE PRESENT INVENTION

Figure 1:
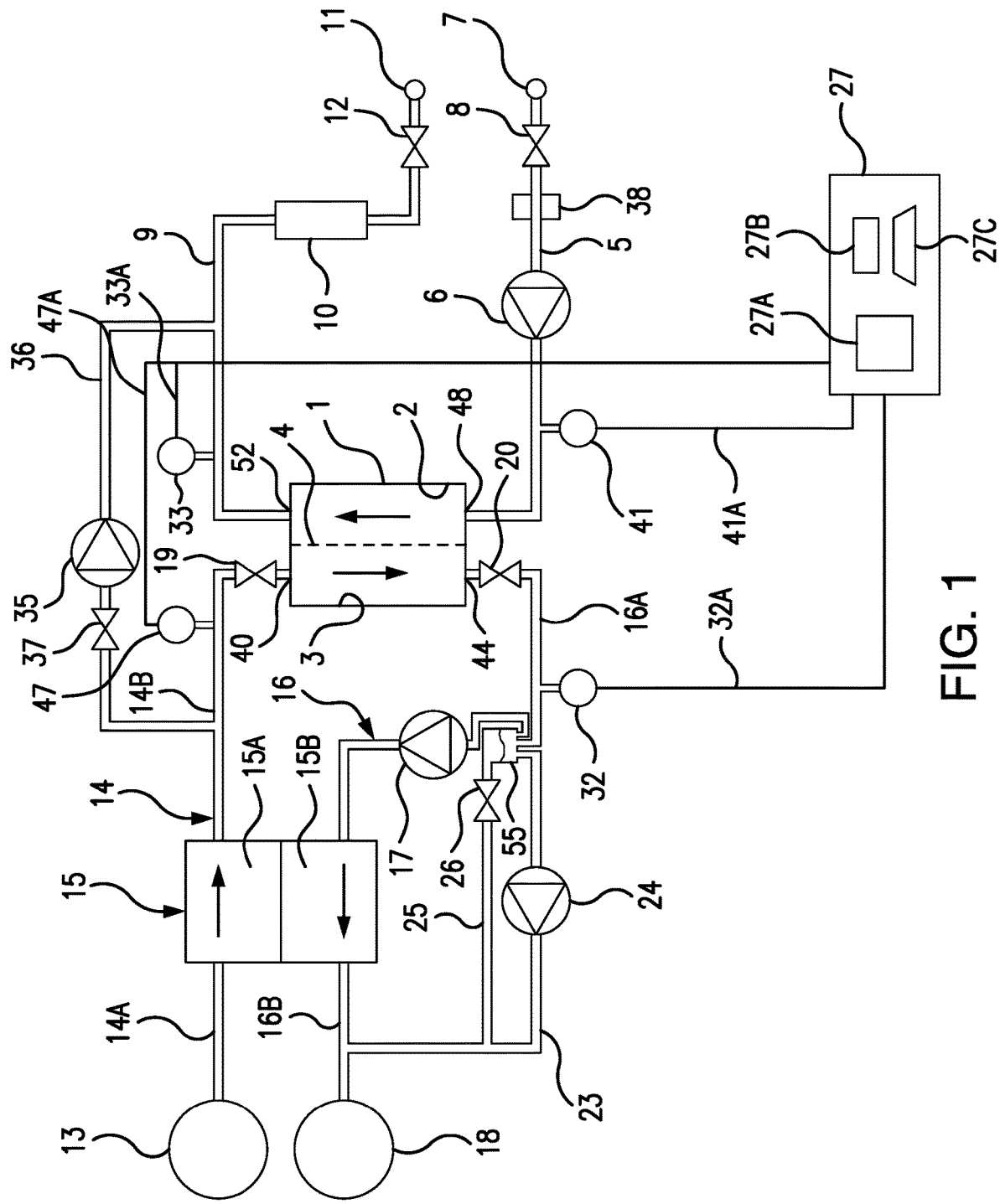
FIG. 1 is a schematic view of an extracorporeal blood treatment device according to an embodiment of the present invention.

The present invention includes an extracorporeal blood treatment device and a method of treatment using the extracorporeal blood treatment device. The extracorporeal blood treatment device includes a dialyzer having a blood chamber, a dialysate chamber, a dialysate inlet, a dialysate outlet, and a semipermeable membrane. The blood chamber and the dialysate chamber being divided from one another by the semipermeable membrane. A dialyzer feed line leads to the dialysate inlet and is configured to supply dialysate to the dialysate chamber. A dialyzer discharge line leads away from the dialysate outlet and is configured to carry dialysate away from the dialysate chamber. A dialysate pump is configured to pump dialysate through the dialyzer feed line to the dialysate chamber and from the dialysate chamber out through the dialyzer discharge line. A dialysate outlet valve can be opened and closed to respectively allow and restrict flow of dialysate from the dialysate chamber of the dialyzer.

The extracorporeal blood treatment device can further include a balancing device having a balancing chamber. A balancing feed line leads to the balancing chamber and is configured to supply fresh dialysate from a dialysate source into the balancing chamber. A balancing discharge line leads away from the balancing chamber and is configured to carry spent dialysate away from the balancing chamber and into a drain. During priming, fresh dialysate can be circulated through different halves of the balancing chamber and can be drained. The dialyzer feed line runs from the balancing chamber and is configured to supply dialysate from the balancing chamber to the dialysate chamber, and the dialyzer discharge line leads to the balancing chamber and is configured to supply dialysate from the dialysate chamber into the balancing chamber.

The extracorporeal blood treatment device is configured to run in a first operating mode and a second operating mode during treatment of a patient or during priming of the device. The first operating mode operates in a configuration in which the dialysate outlet valve is open such that dialysate flows through the dialyzer feed line, through the dialysate chamber, and into and through the dialyzer discharge line. The second operating mode operates in a configuration in which the dialysate outlet valve is closed for a duration of time, dialysate is prevented from flowing through the dialyzer discharge line, and a volume of dialysate passes from the dialysate chamber through the semipermeable membrane and into the blood chamber. During treatment, the backflow of dialysate from the dialysate chamber to the blood chamber through the semipermeable membrane dislodges buildup of secondary membrane, which allows for a more efficient flow through the semipermeable membrane and thus a more efficient treatment of the patient. During priming, the backflow of dialysate from the dialysate chamber to the blood chamber through the semipermeable membrane dislodges buildup of secondary membrane present in reused dialyzers, which also allows for a subsequently more efficient treatment of the patient.

The extracorporeal blood treatment device includes an extracorporeal blood circuit. The extracorporeal blood circuit is in fluid communication with the blood chamber dialyzer via a blood chamber inlet and a blood chamber outlet of the dialyzer. The extracorporeal blood circuit includes a blood pump, a blood supply line that leads to the blood chamber inlet, and a blood removal line that leads away from the blood chamber outlet. The blood pump is configured to pump blood through the blood supply line and the blood chamber inlet into the blood chamber, and out of the blood chamber through the blood chamber outlet and the blood removal line. During treatment of a patient, blood flows through the blood chamber of the dialyzer and dialysate containing desirable matter is introduced into the dialysate chamber of the dialyzer. Undesirable matter from the blood crosses the semipermeable membrane into the dialysate and desirable matter from the dialysate can cross the semipermeable membrane into the blood.

In certain embodiments, the extracorporeal blood treatment device is capable of ultrafiltration. An ultrafiltration line branches off of the dialyzer discharge line downstream of the dialysate outlet valve. An ultrafiltrate pump is disposed on the ultrafiltration line. The ultrafiltrate pump is configured to be switched between an operating state and a non-operating state. During the operating state, the ultrafiltrate pump pulls liquid from the blood chamber, through the semipermeable membrane, into the dialysate chamber, and away from the dialysate chamber through the dialysate outlet valve. Ultrafiltration further increases the removal of undesirable matter from the blood by convection across the semipermeable membrane into the dialysate chamber.

The extracorporeal blood treatment device can further include treatment with substitution fluid. In such embodiments, the extracorporeal blood treatment device includes a substituate line and a substituate pump disposed on the substituate line. In certain embodiments, the substituate line branches off of the dialysate feed line and joins with the blood removal line for post dilution treatment. In other embodiments, the substituate line branches off of the dialysate feed line and joins with the blood supply line for pre dilution treatment. The substituate line can supply a first substituate pump and a second substituate pump disposed on the substituate line, and can join with both the blood supply line and the blood removal line for mixed dilution treatment. The substituate pump can be configured to pump substitution fluid from the dialysate feed line, after passing through a second filter to further remove impurities for example due to direct contact of the substitution fluid with blood, to the blood removal line and/or to the blood supply line, through the substituate line. Substitution fluid can be introduced during hemofiltration treatment in which the blood flows past the semipermeable membrane treatment and desirable matter is added to the blood by dispensing substitution fluid into the blood either before and/or after it passes through the dialyzer with an equal amount of fluid removed from the blood chamber of the dialyzer to maintain fluid volume. The introduction of substitution fluid can also be performed during hemodiafiltration treatment, in which blood and dialysate exchange matter as in hemodialysis, and, in addition, substitution fluid is added to the blood with an equal amount of fluid removed from the blood chamber of the dialyzer to maintain fluid volume.

Each of the pumps and valve(s) of the extracorporeal treatment device can be controlled depending on the type of treatment and whether the extracorporeal treatment device is being run in the first operating mode or the second operating mode. During the first operating mode of a hemodialysis treatment: the dialysate valve is open pending an alarm-free condition; the dialysate pump is activated to continuously pump dialysate through the dialysate chamber; and the blood pump is activated to continuously pump blood through the blood chamber. During the second operating mode of a hemodialysis treatment: the dialysate outlet valve is closed for a duration of time; the dialysate pump speed can be increased, decreased, or maintained at a speed compared to the first operating mode; and the blood pump can be turned off or the blood pump speed can be increased, decreased, or maintained at a speed compared to the first operating mode.

During the first operating mode of a hemofiltration treatment: the dialysate valve is open; the dialysate pump is turned off or operating at a minimal rate, for example, at 100 ml/min; the blood pump is activated to continuously pump blood through the blood chamber; the ultrafiltrate pump is in the operating state in which the ultrafiltrate pump pulls liquid from the blood chamber, through the semipermeable membrane, into the dialysate chamber, and away from the dialysate chamber; and the substituate pump is activated to pump substituate into the blood supply line, the blood removal line, or both. During the second operating mode of a hemofiltration treatment: the dialysate outlet valve is closed for a duration of time; the dialysate pump pumps dialysate through the dialysate chamber; the substitution pump is turned off; the ultrafiltration pump is in the nonoperating state; and the blood pump can be turned off or the blood pump speed can be increased, decreased, or maintained at a speed compared to the first operating mode.

During the first operating mode of a hemodiafiltration treatment: the dialysate valve is open; the dialysate pump is activated to continuously pump dialysate through the dialysate chamber; the ultrafiltrate pump is in the operating state in which the ultrafiltrate pump pulls liquid from the blood chamber, through the semipermeable membrane, into the dialysate chamber, and away from the dialysate chamber; the substituate pump is activated to pump substitution fluid into the blood supply line, the blood removal line, or both; and the blood pump is activated to continuously pump blood through the blood chamber. During the second operating mode of a hemodiafiltration treatment: the dialysate outlet valve is closed for a duration of time; the dialysate pump speed can be increased, decreased, or maintained at a speed compared to the first operating mode; the substitution pump is turned off; the ultrafiltration pump is in the nonoperating state; and the blood pump can be turned off or the blood pump speed can be increased, decreased, or maintained at a speed compared to the first operating mode.

As mentioned above, the second operating mode operates in a configuration in which the dialysate outlet valve is closed for a duration of time, dialysate is prevented from flowing through the dialyzer discharge line, and a volume of dialysate passes from the dialysate chamber through the semipermeable membrane and into the blood chamber. The extracorporeal treatment device can enter the second operating mode multiple times during a treatment, where the duration of each of the second operating modes is relatively short. The timing can be based on the possibility of a dialysate flow rate of from 100 ml/min to 1000 ml/min as is typical on some dialysis machines, for example, the Fresenius Medical Care model 5008s. At a high flow rate of 1000 ml/min, a balancing cycle can take as little as about 2 seconds, and at a low flow rate of 100 ml/min, a balancing cycle can take about 21 seconds. About 15% to 20% can be added to these times to account for the time where the dialysate return line valve is closed. If there is no balancing chamber, only the close time is relevant. Taking into account these considerations, the duration of the second operating mode can range from approximately 0.3-5 seconds if the machine is not equipped with a balancing chamber, and 2-30 seconds if the machine is equipped with a balancing chamber. The duration of the second operating mode can be dependent on the dialysate flow rate to ensure a known volume of fluid is introduced.

Due to the short duration of the second operating mode or modes, a small volume of dialysate can pass from the dialysate chamber through the semipermeable membrane and into the blood chamber. For example, a volume of dialysate that passes into the blood chamber can be from 3 ml to 6 ml, or up to 20 ml. Larger volumes can be used when operating in a priming mode or under conditions causing high secondary membrane formation.

During each second operating mode, a small volume of dialysate passes into the blood stream. The small volume of dialysate can be removed from the blood stream during the subsequent first operating mode of each of the second operating modes. To do so, the ultrafiltration pump can be configured to run at a faster speed during at least a timeframe of the first operating modes (other than the initial first operating mode) to remove a volume of liquid, equivalent to the volume of dialysate introduced in the antecedent second operating mode, from the blood chamber. For example, the ultrafiltrate pump can be configured to remove, for example, a volume of liquid from the blood, which can be from 3 ml to 6 ml, or up to 20 ml. Larger volumes can be removed when operating under conditions causing high secondary membrane formation.

Flow pumps, degassing pumps, auxiliary pumps, combinations thereof, and the like can be used by the extracorporeal treatment device. One or more of such pumps can drive the circulation of fresh dialysate, a cleansing solution, or the like, through the dialysate circuit. The pumps can be controlled to circulate a liquid, for example, a priming solution, a dialysate, a cleaning solution, a rinsing solution, a combination thereof, or the like, through the dialysate circuit.

The extracorporeal blood treatment device of the present invention can include a computing system. The computing system can include a processor, a memory, and a user interface. A data-processing program (software) can be loaded on the memory and run on the processor in order to carry out the method steps. The computing system is in communication with the dialysate pump, the blood pump, the substituate pump, the ultrafiltration pump, the valves, and sensors via wired or wireless communication. The computing system can automatically control the pumps and the valves via the instructions provided by the software, a user can manually control the pumps and valves using the user interface, pre-programmed routines can be run, artificial intelligence can be implemented to better control the treatment and/or future treatments, and the like control features can be implemented.

The sensors can be configured to generate sensor data of the extracorporeal blood treatment device, and the computing system can be configured to use the sensor data to determine when to change the extracorporeal blood treatment device from the first operating mode to the second operating mode, from the second operating mode to the first operating mode, or both. In certain embodiments, the computing system is configured to run the extracorporeal blood treatment device in an initial first operating mode phase for a primary operating time frame, the initial first operating mode phase starting at a beginning of treatment. The primary operating time frame can include from 20 minutes to 80 minutes, 30 minutes to 70 minutes, 40 minutes to 60 minutes, or 50 minutes. When the primary operating time frame expires, the computing system can automatically convert the extracorporeal blood treatment device from the first operating mode to the second operating mode for a secondary operating time frame. The duration of the second operating mode can range from approximately 0.3-5 seconds if the machine is not equipped with a balancing chamber, and 2-30 seconds if the machine is equipped with a balancing chamber. The duration of the second operating mode can be dependent on the dialysate flow rate to ensure a known volume of fluid is introduced. The length of each backflush routine or second operating mode can independently be calculated.

The primary operating time frame can be computed based on a base time that the computing system automatically modifies dependent on at least one device setting variable, such as a plurality of device setting variables. The base time can be pre-set, for example, to be 60 minutes, 70 minutes, 75 minutes, 80 minutes, 90 minutes, or the like.

The device setting variables can include a type of dialyzer that is used during treatment, a type of treatment selected (hemofiltration, hemodialysis, or hemodiafiltration), a substitution pump rate, an ultrafiltration pump rate, a blood pump rate, whether substituate is provided to a blood line upstream or downstream of the dialyzer, a preset ultrafiltration coefficient associated with the dialyzer, an amount of hemodiafiltration bolus, or a combination thereof. The device setting variables are used to determine how much the computing system modifies the base time of the primary operating time frame. For example, if ultrafiltration pump rates, blood pump rates, or a combination thereof are set at an increased rate, the base time is decreased because such changes increase the rate of build-up of secondary membrane. If the substitution fluid flow rate is increased and added post-dilution, the result would be expected to cause more secondary membrane formation.

With the base time decrease, the computing system can switch the extracorporeal blood treatment device from the first operating mode to the second operating mode, sooner, to remove the excess buildup of secondary membrane and maintain efficient treatment. For example, an early backflush may be desirable to better effect the removal of urea. Additionally, the type of treatment can affect the rate of build-up of secondary membrane. For example, secondary membrane can build-up at a faster rate during hemofiltration and hemodiafiltration as compared with hemodialysis if substitution fluid is introduced into the blood after the dialyzer. Alternatively, secondary membrane formation can build-up at a slower rate during hemofiltration and hemodiafiltration as compared with hemodialysis if substitution fluid is introduced into the blood before the dialyzer due to the dilution of the blood. Accordingly, the computing system adjusts the base time during hemodiafiltration or hemofiltration as compared to hemodialysis, for example, based on device setting data input before, at the time of, or during treatment.

During the course of treatment, the computing system periodically receives sensor data from the sensors. Using the sensor data, the computing system can determine device output variables and adjust the base time of the primary operating time frame based on the device output variables. In certain embodiments, the sensors sense levels of urea and pressure in dialysate lines and blood lines of the extracorporeal blood treatment device and the sensor data is provided to the computing system. The computing system can determine device output variables of a venous pressure, a transmembrane pressure, a change in ultrafiltration coefficient, a change in hematocrit, a change in transmembrane pressure, a change in clearance, or a combination thereof using the sensor data. The computing system can then adjust the base time of the primary operating time frame based on the device output variables. For example, if a transmembrane pressure is detected to increase, an ultrafiltration coefficient is detected to decrease, or a combination thereof, the computing system can decrease the base time based on the acquired device output variables. This is because an increase in transmembrane pressure and a decrease in the ultrafiltration coefficient indicate a higher build-up of secondary membrane and thus the need for the second operating mode to be turned on sooner.

In certain embodiments, the duration of time where the dialysate outlet valve is closed during secondary operating time frame of the second operating mode can include a base volume to be delivered from the dialysate chamber into the blood chamber of the dialyzer. The duration of time where the dialysate outlet valve is closed would firstly depend on the dialysate flowrate to ensure the base volume is delivered from the dialysate chamber to the blood chamber of the dialyzer. Moreover, the base volume to be delivered from the dialysate chamber into the blood chamber of the dialyzer itself can be automatically modified by the computing system dependent on device setting variables and device output variables. Similar to modifications to the primary operating time frame, examples of device setting variables can include a type of dialyzer that is used during treatment, a type of treatment selected (hemofiltration, hemodialysis, or hemodiafiltration), a blood pump rate, a substitution pump rate, an ultrafiltration pump rate, or a combination thereof. If substituate pump rates, ultrafiltration pump rates, blood pump rates, or a combination thereof are increased, the base volume to be delivered into the blood chamber of dialyzer during the secondary operating time frame can be increased because such device settings can increase the rate of build-up of secondary membrane. Thus, the base volume to be delivered into the blood chamber of the dialyzer during the secondary operating time frame can be increased so that the computing system can maintain the extracorporeal blood treatment device in the second operating mode for a longer timeframe to remove the excess buildup of secondary membrane to maintain efficient treatment. Examples of device output variables can include a venous pressure, a transmembrane pressure, a change in ultrafiltration coefficient, a change in hematocrit, a change in transmembrane pressure, a change in clearance, or a combination thereof determined by the computing system using the sensor data of the sensors. The computing system can then adjust the base volume to be delivered into the blood chamber of the dialyzer during the secondary operating time frame based on the device output variables. For example, if a transmembrane pressure is detected to increase, an ultrafiltration coefficient is detected to decrease, or a combination thereof, the computing system can increase the base volume to be delivered into the blood chamber of the dialyzer during the secondary operating mode based on the acquired device output variables. This is because an increase in transmembrane pressure and a decrease in the ultrafiltration coefficient indicate a higher build-up of secondary membrane and thus the need for the second operating mode to deliver a larger volume of fluid from the dialysate chamber to the blood chamber of the dialyzer.

In certain embodiments, the computing system is configured to switch the extracorporeal blood treatment device in an alternating sequence between the first operating mode and the second operating mode at a predetermined frequency over a course of a treatment. Each of the plurality of operating modes include a respective operating time frame. The computing system is configured to modify each of the respective operating time frames and, thus the frequency, based on the device setting variables, the device output variables, or both. For example, if ultrafiltration pump rates, blood pump rates, or a combination thereof are set at an increased rate, the base time is decreased because such changes increase the rate of build-up of secondary membrane. If the substitution fluid flow rate is increased and added post-dilution, the result would be expected to cause more secondary membrane formation. Additionally, if the device output variables including a transmembrane pressure is detected to increase, an ultrafiltration coefficient is detected to decrease, or a combination thereof, the computing system can increase the frequency of the secondary operating time frame because an increase in transmembrane pressure and a decrease in the ultrafiltration coefficient indicate a higher build-up of secondary membrane and thus the need for the second operating mode to be operated at a higher frequency.

The computing system can modify the frequency between the first operating mode and the second operating mode of the extracorporeal blood treatment device by comparing ultrafiltration coefficients, transmembrane pressures, or a combination thereof to initial calculated values. For example, the computing system can determine the ultrafiltration coefficient, the transmembrane pressure, or both at a beginning of treatment or within 1 minutes to 20 minutes, within 5 to 15 minutes, or within 10 minutes after the beginning of treatment to determine the initial calculated values. If the ultrafiltration coefficient, the transmembrane pressure, or both are determined after a significant delay from the beginning of treatment, the initial calculated values of the ultrafiltration coefficient and the transmembrane pressure can be modified accordingly. For example, a 33% drop typically occurs of the ultrafiltration coefficient in the first 30 minutes of treatment. For initial calculated values that were calculated after 10 minutes, the following formula can be used to adjust the initial calculated values: Adjusted ultrafiltration coefficient initial calculated value=(ultrafiltration coefficient initial calculated value@time t)*(1+(0.33*(time t)/30)) for t less than 30. If the ultrafiltration coefficient initial calculated value occurred after 30 minutes, use 1.33 as the multiplier.

After the computing system switches the extracorporeal blood treatment device from the first operating mode to the second operating mode and then back to the first operating mode, the ultrafiltration coefficient, the transmembrane pressure, or both can be determined by the computing system again using the sensors and then these values can be compared to the initial calculated values to determine an extent of removal of secondary membrane. If it is determined that the secondary membrane build up is not properly removed, the computing system can adjust the frequency and time frames of the first operating mode and the second operating mode of the extracorporeal blood treatment device. The ultrafiltration coefficient, the transmembrane pressure, or both can be determined by the computing system each time after the second operating mode is switched back to the first operating mode to determine if any adjustments to the frequency and time frames need to be made.

The number of and timing of each backflush can be independently determined and based on initial setting, device output data, rates of change, combinations thereof, or the like. The duration of the second operating mode or backflush can range from approximately 0.3-5 seconds if the machine is not equipped with a balancing chamber, and 2-30 seconds if the machine is equipped with a balancing chamber. The duration of the second operating mode can be dependent on the dialysate flow rate to ensure a known volume of fluid is introduced. Control signals received from the computing system can control the valves, pumps, or a combination thereof to initiate a backflush, to maintain a backflush time, to end a backflush, and/or to switch back to a first operating mode.

The present invention also enables an existing extracorporeal blood treatment device to be programmed with a computer program, set of instructions, algorithm, combination thereof, or the like, as described herein. New or existing devices and processors, for example, comprising or controlling existing valves, pumps, and sensors, can be configured, programmed, or both, to carry out methods and treatments according to the present invention.

FIG. 1 is a schematic diagram showing various components of an extracorporeal blood treatment device with which the present teaching can be implemented. The extracorporeal blood treatment device includes a blood circuit and a dialysate circuit. The blood circuit and the dialysate circuit, together with a dialyser 1, form a fluid system of the extracorporeal blood-treatment device. Dialyzer 1 has a blood chamber 2 and a dialysate chamber 3 that are separated by a semi-permeable membrane 4. A blood supply line 5, along which a blood pump 6 is provided, leads from an arterial patient port 7 to a blood inlet 48 of blood chamber 2. An arterial valve 8 can be located along blood supply line 5, upstream of blood pump 6. A blood removal line 9, in which a liquid chamber 10 can be arranged, leads from a blood outlet 52 of blood chamber 2 to a venous patient port 11. A venous valve 12 can be situated along blood removal line 9, downstream of liquid chamber 10.

The dialysate circuit has a dialysate source 13 for providing fresh dialysate. Dialysate source 13 is connected via a first portion 14A of a dialysate supply line 14 to the inlet of a first chamber 15A of a pair 15 of balancing chambers. A second portion 14B of dialysate supply line 14 connects the outlet of first chamber 15A to a dialysate inlet 40 of dialysate chamber 3. The fresh dialysate can be used as a flushing or preparation liquid. A dialysate outlet 44 of dialysate chamber 3 is connected via a first portion 16A of a dialysate removal line 16 to the inlet of a second chamber 15B of balancing chamber 15. A dialysate flow pump 17 is disposed along first portion 16A of dialysate removal line 16. An outlet of second chamber 15B is connected via a second portion 16B of dialysate removal line 16, to a drain 18. Balancing chamber 15 can have more than two chambers.

A dialysate inlet valve 19 is located along dialysate supply line 14 upstream of dialysate chamber 3. A dialysate outlet valve 20 is located along dialysate removal line 16 downstream of dialysate chamber 3. An air separation chamber or air separator 55 can be disposed along first portion 16A of dialysate removal line 16, downstream of dialysate outlet valve 20 and upstream of dialysate pump 17. The water level in air separator 55 is shown in FIG. 1. Dialysate inlet valve 19 and dialysate outlet valve 20 can be electromagnetically actuatable valves.

An ultrafiltrate line 23 branches from air separator 55 to second portion 16B of dialysate removal line 16. An ultrafiltrate pump 24 is provided along ultrafiltrate line 23. An air removal line 25, along which a bypass valve 26 is provided, leads from the top of air separator 55 to a second portion 16B of dialysate removal line 16. Blood pump 6, dialysate pump 17, and ultrafiltrate pump 24 can be occlusive pumps. If the pumps are occlusive pumps, certain valves for creating a closed volume can be omitted.

The extracorporeal blood treatment device can also have a substitute pump 35 for pumping substitute, also referred to herein as substitution fluid, to the extracorporeal blood circuit upstream or downstream of blood chamber 2, via a substitute line 36. A substitute valve 37 can be provided along substitute line 36, for example, as shown in FIG. 1, upstream of substitute pump 35. Whether the substitution fluid is injected into the extracorporeal blood circuit upstream or downstream of the blood chamber can make a difference on the build-up of secondary membrane. The difference in build-up resulting from the two different injection points can be taken into account through the application of a respective coefficient of modification, as described herein. Whether substitution fluid is injected continuously or as a bolus, into the extracorporeal blood circuit, and upstream or downstream of the blood chamber, can also make a difference on the build-up of secondary membrane. The difference in build-up resulting from the two different injection points of a bolus can be taken into account through the application of a respective coefficient of modification, as described herein.

The extracorporeal blood-treatment device can include a computing system 27 for controlling the pumps and the valves. Computing system 27 can include, for example, a general processor 27A, a digital signal processor (DSP) for continuously processing digital signals, a microprocessor, an application-specific integrated circuit (ASIC), an integrated circuit consisting of logic elements, a field programmable logic array (FPGA), or other integrated circuits (IC) or hardware components for carrying out the individual method steps described herein. Computing system 27 further includes a memory 27B that stores a data-processing program (software) that can run on the hardware components in order to carry out the method steps. Computing system 27 further includes a user interface 27C. User interface 27C can include hardware, software, firmware, or a combination thereof to enable a user to communicate and send commands to computing system 27. For example, user interface 27C can include, but is not limited to, a display, a touch-screen display, a keyboard, a keypad, a mouse, a virtual reality interface, an augmented reality interface, a voice command interface, one or more speakers, one or more microphones, combinations thereof, and the like.

Computing system 27 is connected to dialysis pump 17, blood pump 6, ultrafiltrate pump 17, substitute pump 35, dialysate inlet valve 19, dialysate outlet valve 20, blood inlet valve 8, blood outlet valve 12, bypass valve 26, and substituate valve 37, via control lines or data lines (not shown), so that the flow rates of the pumps can be set and the valves and bypass valves can be actuated, via the computing system 27. The valves and bypass valves have actuating members (not shown) that can act on the fluid lines.

The extracorporeal blood-treatment device can further include sensors 32, 33, 41, and 47 that are connected to computing system 27 via data lines 32A, 33A, 41A, and 47A, respectively. Sensor 47 is a dialysate supply pressure sensor that measures pressure within dialysate supply line 14. Sensor 32 is a dialysate removal pressure sensor that measures pressure within dialysate first portion 16A of the dialysate removal line. Sensor 41 is a blood supply pressure sensor that measures blood pressure within blood supply line 5 downstream of blood pump 6. Sensor 33 is a blood removal pressure sensor that measures pressure within blood removal line 9. Sensors 32, 33, 41, and 47 measure pressure within their respective fluid lines and generate sensor data that is sent to and processed by computing system 27. Computing system 27 can determine transmembrane pressure, ultrafiltration coefficients, and other values using the sensor data. The sensors can also include a urea sensor, an air separator pressure sensor, and the like sensors, that can be used in an extracorporeal blood-treatment device. Sensors 41 and 47 can optionally be included, for example, to improve accuracy of the calculated transmembrane pressure and calculated ultrafiltration coefficient during treatment.

Sensors 32, 33, 41, and 47 are configured to generate sensor data of the extracorporeal blood treatment device, and computing system 27 is configured to use the sensor data to determine when to change the extracorporeal blood treatment device from the first operating mode to the second operating mode and from the second operating mode to the first operating mode.

In use, a user can start by entering device setting variables into computing system 27, or device setting variables can be preloaded into computing system 27. Device setting variables can include, but are not limited to, a type of dialyzer that is used during treatment, a type of treatment selected (for example, hemofiltration, hemodialysis, or hemodiafiltration), a substitution fluid pump rate, an ultrafiltration pump rate, a blood pump rate, whether substituate is provided to a blood line upstream or downstream of the dialyzer, a preset ultrafiltration coefficient, an amount of hemodiafiltration bolus, whether a bolus in injected predilution or postdilution, and combinations thereof. Computing system 27 can modify the base time of a primary operating time frame, the base time of a secondary operating time frame, or a combination thereof, based on the device setting variables. To begin a treatment, arterial patient port 7 and venous patient port 11 are connected to a patient and the extracorporeal blood treatment device begins treatment in the first operating mode for the modified primary operating time frame. Once the modified primary operating time frame has expired, computing system 27 can switch the extracorporeal blood treatment device to the second operating mode for the modified second operating time frame.

While the extracorporeal blood treatment device is running, computing system 27 is periodically receiving sensor data from sensors 32, 33, 41, and 47. Using the sensor data, computing system 27 can determine device output variables and adjust the base time of the primary operating time frame and of the secondary operating time frame based on the device output variables. In certain embodiments, sensors 32, 33, 41, and 47 sense levels of clearance and pressure in dialysate lines 14 and 16 and in blood lines 5 and 9 of the extracorporeal blood treatment device, and the sensor data can be sent to computing system 27. Computing system 27 then determines device output variables and selects predetermined coefficients or modification based on venous pressure, transmembrane pressure, changes in ultrafiltration coefficient, changes in hematocrit, changes in transmembrane pressure, changes in clearance, combinations thereof, and the like, using the sensor data. Along blood line 5 a fluid management monitoring tool can be attached that, for example, incorporates photo-optical technology to non-invasively measure absolute hematocrit and continuous oxygen saturation. In addition, such an attached device, commonly referred to as a CLiC, can also be configured to calculate the percent change in the dialysis patient's intravascular blood volume and oxygen saturation. Computing system 27 can then adjust the base time of the primary operating time frame and the secondary operating time frame based on the device output variables.

As an example, if a transmembrane pressure is detected as increasing, or an ultrafiltration coefficient is detected as decreasing, or a combination thereof, computing system 27 can decrease the base time based on the acquired device output variables. Decreasing the base time can be carried out based on the conclusion that an increase in transmembrane pressure and a decrease in ultrafiltration coefficient indicate a build-up of secondary membrane on the dialyzer semipermeable membrane, and thus indicate a need for the second operating mode to be run sooner, for a longer time frame, or both.

FIGS. 2A and 2B show a device setting variable table having four columns including the type of device setting variable, a discrete modifier, a percent modifier, and a coefficient of modification. The type of device setting variable is a variable set by a user of the device, or by the computing system, prior to or during treatment of a patient. The discrete modifier, the percent modifier, and the coefficient of modification are pre-programmed data points used by the computing system to adjust the base time before switching to the second operating mode, based on the entered device setting variables. Specifically, the discrete modifier is an amount of time, in minutes, that the computing system subtracts from or adds to the base time. The percent modifier is a percentage of the base time that the computing system deducts from or adds to the base time. The coefficient of modification is the coefficient used by the computing system to adjust the base time and to thereby determine a time interval before each second operating mode (backflush). The coefficient of modification is calculated based on the percent modifier and is not used when discrete modifiers are subtracted from or added to the base time. The coefficients of modification and equations using them are explained in more detail below.

Examples of the type of device setting variables include a substitution fluid rate, an ultrafiltrate (UF) rate, and a blood flow rate. A user or the computing system can set the substitution fluid rate, the UF rate, and the blood flow rate. The computing system can then deduct or add time to the base time to determine when the computing system can switch the blood extracorporeal device from the first operating mode to the second operating mode to backflush the semipermeable membrane. For example, if the blood flow rate is set at 200 ml/min, the percent modifier is −3% and thus a 3% reduction in time of the base time is calculated. Likewise, if a UF rate is set at 2000 ml/hour, the percent modifier is −10%, and thus a 10% reduction in time of the base time is calculated. Increased flow rates of ultrafiltrate, and blood, cause a higher rate of secondary membrane build up, and thus would make it desirable to backflush the semipermeable membrane earlier, rather than later, during the course of a treatment.

Other examples types of device setting variables included in the table of FIGS. 2A and 2B include the type of dialyzer used in the extracorporeal blood treatment device (OPTIFLUX and Dialyzer (Custom)), the hemodiafiltration bolus amount, the change (Δ) in ultrafiltration rate, the change (Δ) in blood flow rate, and the change (Δ) in substitution fluid rate. For these examples, a discrete modifier and a percent modifier are provided. If the type of device setting includes both a discrete modifier and a percentage modifier, only one of the modifiers is applied. For example, the greater of the two can be applied to the base time based on the remaining time until switching from the first operating mode to the second operating mode. For example, if an OPTIFLUX 250 NR dialyzer is being used in the extracorporeal treatment device, the discrete modifier is −4 minutes and the percent modifier is −10%. If the base time is 60 minutes, a deduction of 10% is equal to a subtraction of 6 minutes (−6 minutes). The discrete modifier of −4 minutes is less than −6 minutes in absolute value, and thus the % modifier of −10% would be applied to the base time to determine the time interval.

The table in FIG. 2B also shows a modifier for predilution and for postdilution of substitution fluid into the blood. Predilution is when substitution fluid is pumped into the blood line upstream of the dialyzer, while postdilution is when substitution fluid is pumped into the bloodline downstream of the dialyzer. As shown in the table of FIG. 2B, for predilution, the substitution fluid rate percent modifier is multiplied by −1, and for postdilution, the substitution fluid rate modifier is multiplied by 1. By multiplying the substitution fluid rate modifier by −1, the negative percent modifier for the substitution fluid rate becomes a positive percent modifier and thus increases the base time instead of decreasing the base time. This is because higher rates of prediluted blood flowing through the dialyzer reduces a rate of secondary membrane formation on the semipermeable membrane. Accordingly, as shown in FIGS. 2A and 2B if the substitution flow rate is set at 100 ml/min, the percent modifier is −2% and thus a 2% reduction in time of the base time is calculated for a postdilution HF or HDF therapy, and a +2% or 2% increase in the time of the base time is calculated for a predilution HF or HDF therapy. Likewise, for a predilution HF or HDF therapy, an increase in the substitution fluid rate of more than 100 ml/min would result in modifiers to the base time of +4 minutes or +10% instead of −4 minutes or −10% as would be used for a postdilution HF or HDF therapy.

FIG. 3 is a table of device output variables and has four columns, including the type of device output variable, a discrete modifier, a percent modifier, and a coefficient of modification. The device output variables are based on sensed readings from the sensors of the extracorporeal blood treatment device, sensed during the treatment of the patient. Thus, the device output variables are distinguished from the device setting variables because the device output variables are dynamically detected by the computing system, in real-time, whereas the device setting variables are set by a user or the computing system prior to or at the beginning of a treatment. The discrete modifier is an amount of time in minutes that is subtracted from or added to the base time and the percent modifier is a percentage of time deducted from or added to the base time. The coefficient of modification is the coefficient used in the equation to adjust the base time and determine a time interval before each second operating mode (backflush).

The table in FIG. 3 provides exemplary percentage deductions and each corresponding coefficient of modification for ranges of detected venous pressure and detected transmembrane pressure. The table in FIG. 3 further provides exemplary minute deductions and percentage deductions for changes (Δ) in ultrafiltration coefficient, changes (Δ) in hematocrit (Hct) concentration, changes (Δ) in transmembrane pressure, and changes (Δ) in clearance (K). Deltas are sensed variables that are compared with sensed variables taken at the beginning or near the beginning of treatment. If the type of device output variable includes both a discrete modifier and a percentage modifier, only one of the modifiers is applied. For example, the modifier that provides the greater of the two additions or subtractions, is applied to the base time. If the discrete modifier is applied, the coefficient of modification is ignored.

To provide a few examples of how to modify a base time to obtain a time interval before backflush, using the tables of FIGS. 2A, 2B, and 3, the following equation can be used:

$$T_i = T_B \cdot R_n \cdot Q_s \cdot Q_{uf} \cdot Q_b \cdot X_d \cdot P_v \cdot P_{tm} \quad \text{Equation I}$$

wherein $T_i$ is time interval before a backflush, $T_B$ is the base time, $R_1$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, and $P_{tm}$ is the cm based on the transmembrane pressure.

Example 1: In this exemplary embodiment, the base time ($T_B$) is set to 60 minutes. The device setting variables of the extracorporeal blood treatment device can be set to include the following. The substitution flow rate can be set to 200 ml/min. The percent modifier for 200 ml/min of substitution rate is −4% and thus the coefficient of modification for $Q_s$ is 0.96. The extracorporeal blood treatment device can be set for hemodiafiltration treatment in which substitution fluid is introduced to the blood line upstream of the dialyzer, i.e., predilution. For predilution, the percent modifier of the substitution flow rate is multiplied by −1, such that the percent modifier equals +4%. To determine $Q_s$ for a predilution treatment, an intermediate variable $Q_{sn}$ ($Q_s$ normal) is used equal to the $Q_s$ value that would be used in a postdilution treatment, and a modified value $Q_{sm}$ ($Q_s$ modified) is then calculated. To calculate $Q_{sm}$, the equation used is: $Q_{sm} = 2 - Q_{sn}$. Thus, for this particular example with a predilution treatment modality, $Q_s = Q_{sm} = 2 - 0.96$, which is 1.04. The ultrafiltration rate can be set at 1250 ml/hr. The percent modifier for 1250 ml/min of ultrafiltration rate is −6% and thus the coefficient of modification $Q_{uf}$ is 0.94. The blood flow rate can be set at 200 ml/min. The percent modifier for a blood flow rate of 200 ml/min is −3%, such that $Q_b$ is 0.97. When an OPTIFLUX 160NR dialyzer is used for the extracorporeal blood treatment, the table shows a percent modifier of zero (0) for an OPTIFLUX 160NR dialyzer, thus, $X_d$ is 1.

The device output variables of the extracorporeal blood treatment device can be detected during treatment as follows. The computing system can detect that treatment has just begun and thus is considered the first run. The percent modifier for the first run is −40% and thus $R_n$ is equal to 0.6. Pressure sensors can detect that the venous pressure is 250 mmHg. The percent modifier for a venous pressure sensed at 250 mmHg is −4% and thus $P_v$ is 0.96. Pressure sensors can detect a transmembrane pressure of 250 mmHg. The percent modifier for transmembrane pressure sense at 250 mmHg is −6% and thus $P_{tm}$ is 0.94. which is a −6% modifier.

With $T_B$ equaling 60 minutes, $R_n$ equaling 0.6, $Q_s$ equaling 1.04, $Q_{uf}$ equaling 0.94, $Q_b$ equaling 0.97, $X_d$ equaling 1, $P_v$ equaling 0.96, $P_{tm}$ equaling 0.94, each of the coefficients of modification is entered into Equation 1, that is, entered into the equation $T_i = T_B \cdot R_n \cdot Q_s \cdot Q_{uf} \cdot Q_b \cdot X_d \cdot P_v \cdot P_{tm}$ to determine the time internal $T_i$ for the first run, which is the time interval from the beginning of treatment until the first backflush, that is, the time of operating in the first operating mode before switching to the second operating mode. Thus, the equation to calculate the first time interval would be 60 minutes times (·): 0.6·1.04·0.94·0.97·1.0·0.96·0.94=30.8. Thus, $T_i$ for the first run would equal approximately 30.8 minutes.

In this example, the first operating mode would initially run for approximately 30.8 minutes on the extracorporeal blood treatment device. Once the 30.8-minute time interval expires, the computing system switches the extracorporeal blood treatment device from the first operating mode to the second operating mode to run a backflush and dislodge secondary membrane buildup.

Example 2: After running the second operating mode for a certain timeframe, for example, based on a second base time of five seconds, the computing system switches the extracorporeal blood treatment device back to the first operating mode for a modifiable base time of 60 minutes. The base time is again adjusted based on the device setting variables and the device output variables. For the second time frame operating in the first operating mode, the machine setting variables would generally be the same as in the example mentioned above, except there would be no 40% reduction based on the first run, run number, coefficient of modification. For the second run, the run number coefficient of modification for the run number modifier is 1.0, that is, there is no change to the base time based on run number; the base time is not reduced by 40% because the second run would be a subsequent run, not the first run. Thus, the equation for calculating the second iteration of the first operating mode is as follows: 60 minutes times (·) 1.04·0.94·0.97·1.0·0.96·0.94=51.34 minutes. Thus, approximately 51.34 minutes after switching from the second operating mode back to the first operating mode, a backflush is again carried out, run, or performed. This second time interval, can be adjusted based on one or more variables and/or changes and application of the corresponding coefficients of modification shown in the tables of FIGS. 2A, 2B, and 3.

Example 3: The 51.34 minutes calculated above in example 2 would define the second time interval in the first operating mode, under generally normal conditions. If, however, during the second time interval in the first operating mode, it is determined that the ultrafiltration coefficient has decreased by more than 15% at, for example, 30 minutes after the second entry into the first operating mode, and further the transmembrane pressure has increased by more than 5% at 15 minutes after the second entry into the first operating mode, two additional time interval reductions (modifications) would be made. As shown in the table of FIG. 3, these two device output variables would each dictate that either a four-minute discrete modifier or a −10% modifier should be applied.

With respect to the decrease in the ultrafiltration coefficient, if it were detected 30 minutes after the second entry into the first operating mode, approximately 21.34 minutes would have originally been left before the second entry into the second operating mode. The −10% reduction corresponds to a coefficient of modification value: $\Delta UFC_{cm}=0.9$. A comparison is made of the discrete modifier value and the to be applied % value using the following formula: % time value to be applied=(Remaining Time)*(1−Coefficient of Modification). For ΔUFC, the % time value to be applied is: (21.34 minutes)*(1−0.9)=2.134 minutes. Then, because 4 minutes is greater than 2.134 minutes, the discrete modifier is used for the detected decrease in the ultrafiltration coefficient. Using the same comparison method, for the increase in transmembrane pressure 15 minutes after the second entry into the first operating mode the % time value to be applied is calculated as: (51.34 minutes−15 minutes)*(1−0.9)=3.634 minutes. Again, it is the case that the discrete modifier of 4 minutes is greater, and therefore, is used, and as a result a total of eight minutes would be subtracted from the 51.34-minute interval. The eight minutes would result from, when using the table shown in FIG. 3, a four-minute reduction based on ΔUFC and a four-minute reduction based on ΔTMP, totaling the eight-minute reduction. As a result, the control system would cause the system to perform a backflush after a modified time interval of 43.34 minutes, not 51.34 minutes. Under such circumstances, the second iteration of the first operating mode would last for 43.34 minutes. Accordingly, under such circumstances where a coefficient of clearance, a transmembrane pressure, a combination thereof, or the like, changes significantly during a treatment, Equation II is then used for calculating the second time interval, and is shown here when it is determined only discrete modifiers are applied:

$$T_i = (T_B \cdot R_n \cdot Q_s \cdot Q_{uf} \cdot Q_b \cdot X_d \cdot P_v \cdot P_{tm}) + \text{Mod}_X \quad \text{Equation II}$$

wherein $T_i$ is time interval before a backflush, $T_B$ is the base time, $R_n$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, $P_{tm}$ is the cm based on the transmembrane pressure, and $\text{Mod}_X$ is the sum of discrete modifiers to be taken into consideration. In Example 3 above, $\text{Mod}_X$ is the sum of the discrete modifier ΔTMP (5%) and the discrete modifier ΔUFC>15% (decrease). From FIG. 3, it can be seen that ΔTMP (5%) is equal to −4 minutes and ΔUFC>15% (decrease) is equal to −4 minutes. Thus, $\text{Mod}_X$ is −8 minutes. Accordingly, the processor subtracts eight minutes from $T_i$ relative to what would otherwise have been calculated based only on the coefficients of modification $T_B$, $R_n$, $Q_s$, $Q_{uf}$, $Q_b$, $X_d$, $P_v$, and $P_{tm}$. As a result, and taking into consideration $\text{Mod}_X$, the time interval $T_i$ is 43.43 minutes, not 51.43 minutes. $\text{Mod}_X$ can be any applicable value.

Other coefficients of modification as shown in FIGS. 2A, 2B, and 3 can also be taken into consideration by application of Equation III shown here:

$$T_{i+1} = (T_B \cdot R_n \cdot Q_s Q_{uf} \cdot Q_b \cdot X_d \cdot P_v \cdot P_{tm}) + (-(T_i - T_{Ei}) \cdot (1 - X_A)) + \text{Mod}_X \quad \text{Equation III}$$

wherein $T_{i+1}$ is newly calculated time interval before a backflush, $T_i$ is the originally calculated time interval before a backflush, $T_B$ is the base time, $R_n$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, $P_{tm}$ is the cm based on the transmembrane pressure, $T_{Ei}$ is the elapsed time since the initiation of the current first operating mode, $\text{Mod}_X$ is the sum of discrete modifiers to be taken into consideration, and $X_A$ is an additionally applicable coefficient of modification. The i denoted in $T_{i+1}$, $T_i$, and $T_{Ei}$, indicate the iterative nature of equation III.

Example 4: In an example wherein a decrease in clearance of greater than 15% detected 10 minutes into entry of the second first operating mode, $X_A = \Delta K_{cm} = 0.9$. For simplicity we will assume $R_n$, $Q_s$, $Q_{uf}$, $Q_b$, $X_d$, $P_{tm}$, and $P_v$ equal 1 and therefore $T_i = T_b = 60$ minutes. As in Example 3 above, a comparison is made to determine the greater absolute value of $(-((T_i - T_{Ei}) \cdot (1 - X_A))$ which is herein referred to as the "to be applied % value" and the discrete modifier for the relevant device output or device setting variable. For the device output variable decrease in clearance of greater than 15%, the discrete modifier is −4 minutes. The to be applied % value is calculated as: $(-(60 \text{ minutes} - 10 \text{ minute}) \cdot (1 - 0.9))$ =−5 minutes. Negative five (−5) minutes has a greater absolute value than −4 minutes, thus, the to be applied % value is used in-lieu of the discrete modifier. Accordingly, equation III yields: 60 minutes+(−5 minute)=55 minutes=$T_{i+1}$.

To illustrate the iterative nature of equation III, and in another exemplary case, in addition to the detected decrease in clearance of greater than 15% is detected 10 minutes into entry of the second first operating mode, an increase of hematocrit (Hct) of 15% is detected 13 minutes into entry of the second first operating mode. The to be applied % value for the detected increase in hematocrit is calculated as: $(-(55 \text{ minutes} - 13 \text{ minute}) \cdot (1 - 0.9))$ =−4.2 minutes, and the discrete modifier for the device output variable increase of Hct>15% is −4 minutes. Negative 4.2 (−4.2) minutes has a greater absolute value than −4 minutes, thus, the to be applied % value is used in-lieu of the discrete modifier. Accordingly, equation III yields: 55 minutes+(−4.2 minute) =50.8 minutes=$T_{i+1}$. As a result, the newly calculated time interval $T_{i+1}$ originally calculated as 60 minutes would be reduced twice to a final value of only 50.8 minutes. The second backflush would thus occur more than 9 minutes earlier than if no to be applied % values were introduced.

Equation IV shown below can be used to account for a case wherein a parameter, for example, $Q_s$ or $P_{tm}$, has a change that warrants a change in value of the applied % modifier.

$$T_{i+1} = (T_B \cdot R_n \cdot Q_s \cdot Q_{uf} \cdot Q_b \cdot X_d \cdot P_v \cdot P_{tm}) + ((T_i - T_{Ei}) \cdot ((2 - Y_{Aold}) * Y_{Anew})) - (T_i - T_{Ei})) + (-((T_i - T_{Ei}) \cdot (1 - X_A)) + \text{Mod}_X \quad \text{Equation IV}$$

wherein $T_{i+1}$ is newly calculated time interval before a backflush, $T_i$ is the originally calculated time interval before a backflush, $T_B$ is the base time, $R_n$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, $P_{tm}$ is the cm based on the transmembrane pressure, $T_{Ei}$ is the elapsed time since the initiation of the current first operating mode, $\text{Mod}_X$ is the sum of discrete modifiers to be taken into consideration, $X_A$ is an additionally applicable coefficient of modification, $Y_{Aold}$ is the previously applicable coefficient of modification for $Q_s$, $Q_{uf}$, $Q_b$, $X_d$, $P_{tm}$, or $P_v$ that is observed to have changed, and $Y_{Anew}$ is the newly applicable coefficient of modification for $Q_s$, $Q_{uf}$, $Q_b$, $X_d$, $P_{tm}$, or $P_v$ that is observed to have changed. The i denoted in $T_{i+1}$, $T_i$, and $T_{Ei}$, indicate the iterative nature of equation IV.

Example 5: If the blood flow rate is detected to increase from 125 ml/min to 175 ml/min after being in the second first operating mode for 5 minutes. As in example 4, for simplicity we will assume $R_n$, $Q_s$, $Q_{uf}$, $X_d$, $P_{tm}$, and $P_v$ equal 1. For a blood flow rate of 125 ml/min, $Q_b$ also equals 1, and therefore $T_i = T_b = 60$ minutes. The % modifier contributed by the blood flow rate device setting variable would change from 0% to −3%, and accordingly, $Y_{Aold} = Q_b = 1$ and $Y_{Anew} = 0.97$. A value for $((T_i - T_{Ei}) \cdot ((2 - Y_{Aold}) * Y_{Anew})) - (T_i -$ $T_{Ei}$)), herein referred to as the to be applied modified % value, is calculated: ((60 minutes−5 minutes)·((2−1)*0.97)−(60 minutes −5 minutes))=−1.65 minutes. Accordingly, equation IV yields: 60 minutes+(−1.65 minute)=58.35 minutes=$T_{i+1}$.

To illustrate the iterative nature of equation IV, and in a case where, in addition to the detected increase in blood flow rate from 125 ml/min to 175 ml/min after 5 minutes into entry of the second first operating mode, a decrease in the blood flow rate from 175 ml/min back to 125 ml/min is detected ten minutes into entry of the second first operating mode. Resultant of the second change in blood flow rate, the % modifier contributed by the blood flow rate device setting variable would change from −3% to 0%, and accordingly $Y_{Aold}$=0.97 and $Y_{Anew}$=1. The to be applied modified % value is calculated as follows: ((58.35 minutes−10 minutes)·((2−0.97)*1)−(58.35 minutes−10 minutes))=+1.45 minutes. Accordingly, equation IV yields: 58.35 minutes+(1.45 minute)=59.8 minutes=$T_{i+1}$. Through equation IV, any changes to $Q_b$, $Q_s$, $Q_{uf}$, $X_d$, $P_{tm}$, and $P_v$ that warrants a change in value of the applied % modifier is addressed.

FIGS. 2A, 2B, and 3 are not limiting of the coefficients of modification that can be considered or used for a particular device or method, but are exemplary of numerous coefficients of modification that can be applied. The values for the discrete and % modifiers are not limiting.

To account for adjustments to dialysate flow rate, substitution fluid flow rate, and blood flow rate, and their impact on transmembrane pressure, a modification to the starting TMP value can be made for use when detecting an increase in TMP. If, for example, the TMP was detected to have increased by 2%, and then the blood flow rate, dialysate flow rate, or substitution fluid flow rate was changed, the result would be an associated change to the TMP. A newly stabilized TMP value (after 5 minutes of no change to Qs, Qd, or Qb) would be observed. Based on the previously detected 2% increase in TMP, a modified baseline TMP value would be generated such that: Modified Baseline TMP*(1.02)= (Stabilized Baseline TMP). The Modified Baseline TMP value would then be used as the basis for detecting a ΔTMP that truly warrants a modification to the time interval before a backflush. In so doing, the detection of increases in TMP that would be the basis of adjustment to the calculated time interval before a backflush shown in the bottom rows of FIG. 3 will not be falsely triggered by the adjustment dialysate flowrate, substitution flowrate, or blood flow rate. Changes to the time interval before backflush would not occur unless the Modified Baseline TMP was detected to have increased by 5%, 10%, or 15% and the change would be implemented through equation III through the application of a discrete modifier or a to be applied % value. Any additionally needed change to the calculated time interval before a backflush resultant of the change in value of the device setting variables dialysate flow rate, substitution fluid flow rate, blood flow rate, or the change in value of the device output variable transmembrane pressure would be addressed, as needed, through the to be applied modified % value of equation IV.

Figure 4A:
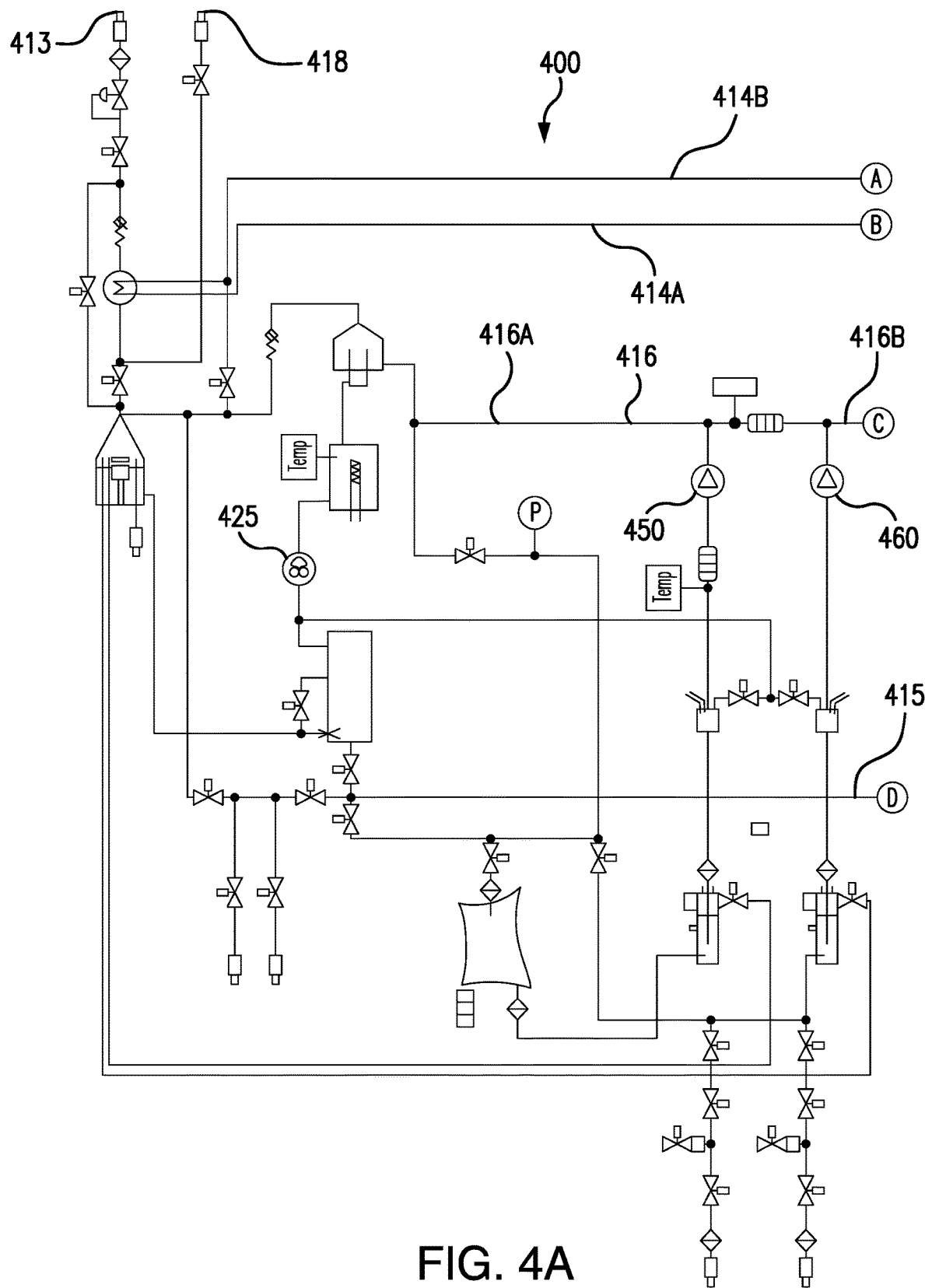
FIGS. 4A and 4B are the left and right portions, respectively, of a schematic diagram of an extracorporeal blood treatment device of an embodiment of the present invention.
Figure 4B:
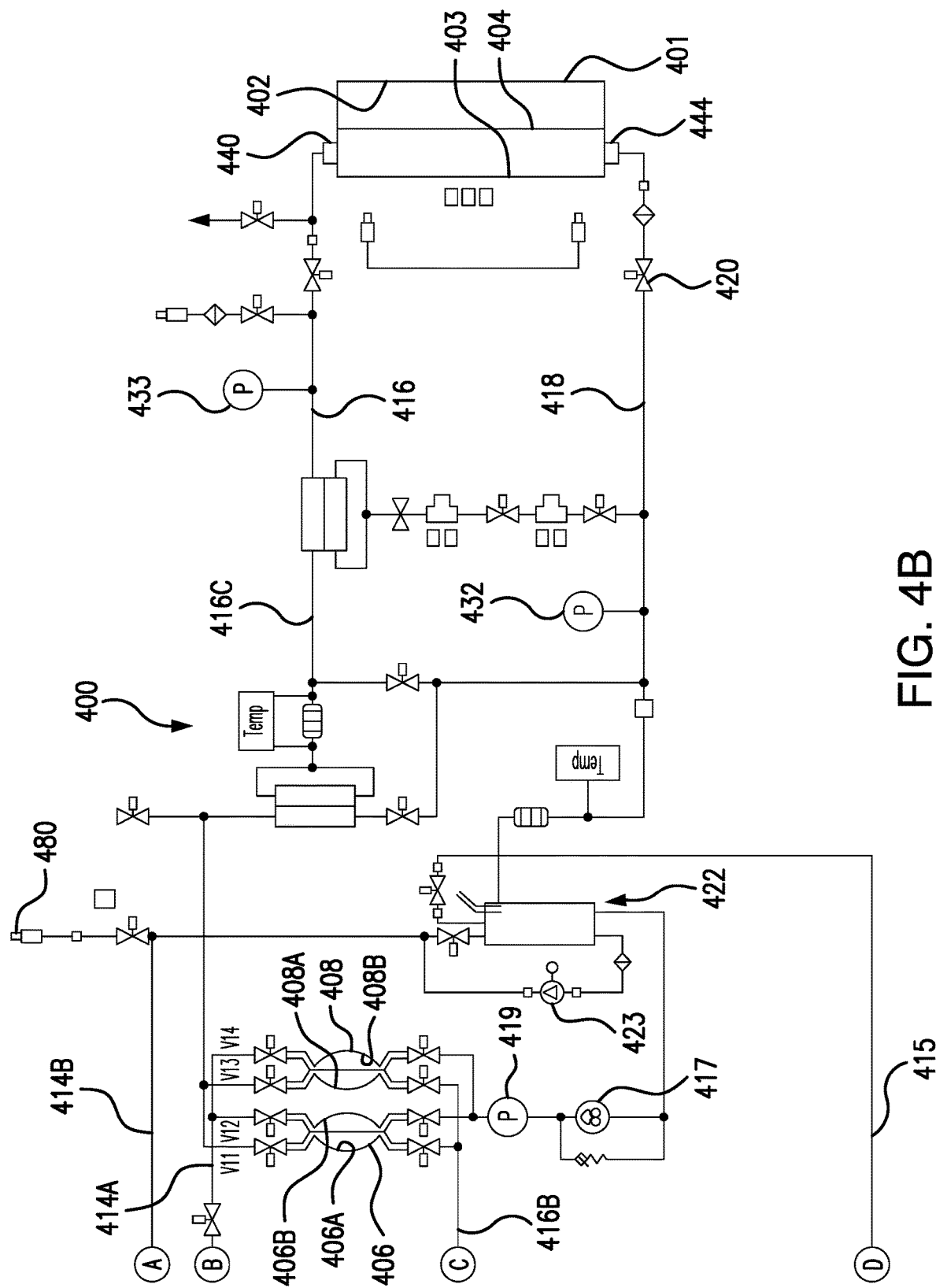

FIGS. 4A and 4B are the left and right portions, respectively, of a schematic view of a dialysate circuit 400 of another embodiment of an extracorporeal blood treatment device. Line terminations A, B, C, and D shown in FIG. 4A continue and are in fluid communication with line terminations A, B, C, and D, respectively, shown in FIG. 4B. The extracorporeal blood treatment device includes a dialyzer 401 that comprises a blood chamber 402 and a dialysate chamber 403 that are separated by a semi-permeable membrane 404. Dialysate circuit 400 includes a water source 413 for making fresh dialysate. Water source 413 is connected via a first portion 416A of a supply line 416 in which water is mixed with bicarbonate supplied by a bicarbonate pump 450, and mixed with electrolytes supplied from a concentrate pump 460, to form dialysate. The dialysate then travels through a second portion 416B of supply line 416 from which the dialysate is moved into the fresh dialysate side 406A of a first balancing chamber 406 and into the fresh dialysate side 408A of a second balancing chamber 408. Fresh dialysate exiting fresh dialysate sides 406A and 408A then makes its way through a third portion 416C of supply line 416 and into a dialysate inlet 440 of dialysate chamber 403. The fresh dialysate can be used as a flushing or preparation liquid. Pressure of dialysate in supply line 416, just prior to entering dialysate chamber 403, can be sensed with a pressure transducer 433 arranged along third portion 416C of supply line 416.

A dialysate outlet 444 of dialysate chamber 403 is connected to a dialysate removal line 418. Spent dialysate, ultrafiltrate, a combination thereof, or fresh dialysate during priming, exits dialysate outlet 444 and moves through dialysate removal line 418. Pressure in dialysate removal line 418 can be sensed by a pressure transducer 432 arranged along dialysate removal line 418.

Through the actions of an ultrafiltrate pump 423 and a flow pump 417, dialysate removed from dialysate chamber 403 can be moved to a drain 480 or into a spent dialysate side 406B and a spent dialysate side 408B of balancing chambers 406 and 408, respectively. A pressure sensor 419 is provided downstream of flow pump 417 and is configured to sense the pressure in the line downstream of pump 417. Ultrafiltrate pump 423 can be part of an ultrafiltration system 422. During priming, dialysate removed along dialysate removal line 418 can be moved, at least in part, by a degassing pump 425 along a dialysate recirculation line 415. A dialysate outlet valve 420 is located along dialysate removal line 418 downstream of dialysate chamber 403 and outlet 444. Dialysate outlet valve 420 remains open during the first operating mode described herein and is closed for a duration of time during the second operating mode described herein.

Figure 5A:
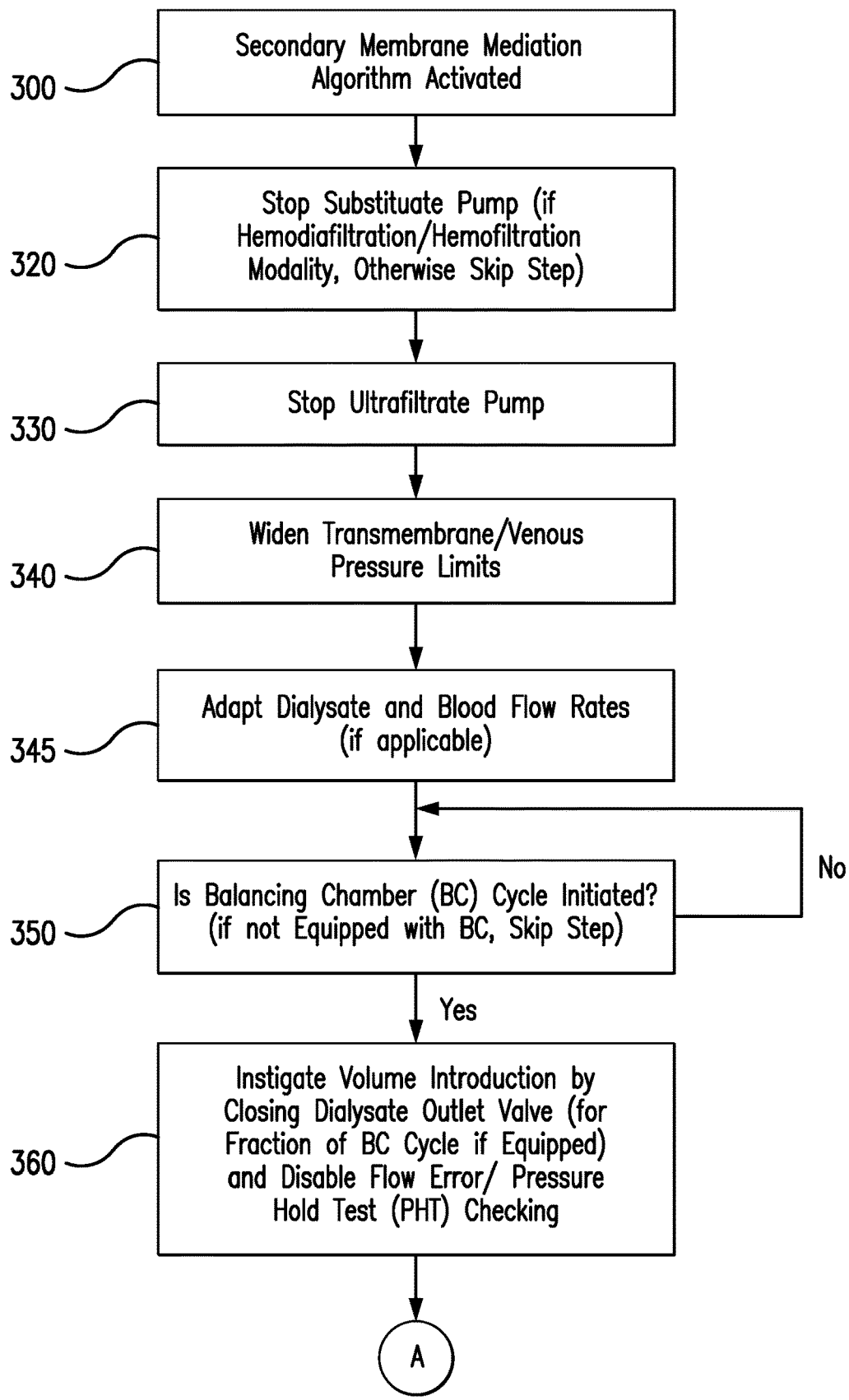
FIGS. 5A and 5B are the top part and bottom part, respectively, of a flow chart showing the method steps to be carried out in accordance with a method according to an embodiment of the present invention.
Figure 5B:
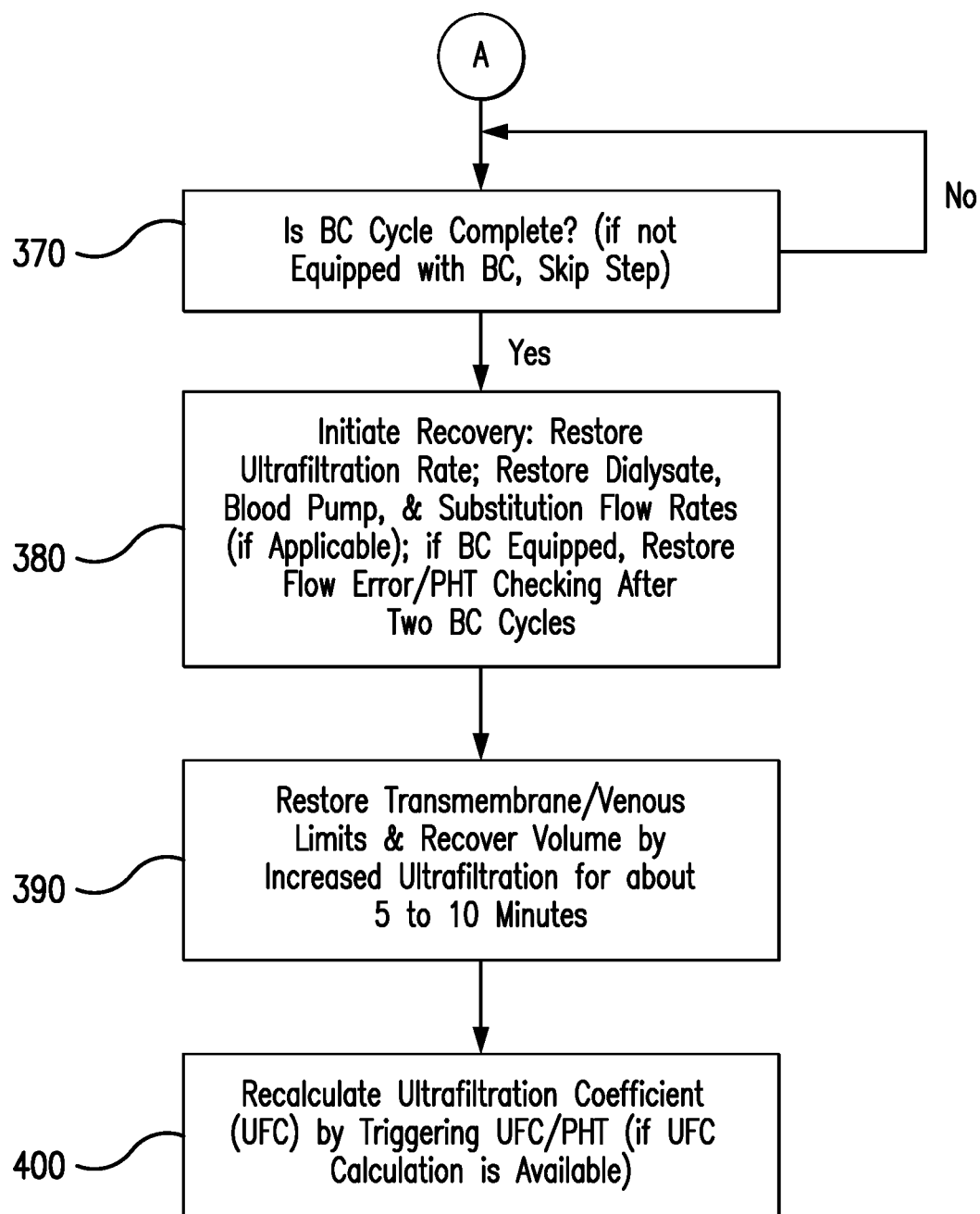

FIGS. 5A and 5B show a flow chart of a method of treatment of a patient using the extracorporeal blood treatment devices of FIG. 1 or 3A and 3B. The extracorporeal blood treatment device begins treatment in the first operating mode. The computing system then activates the secondary membrane mediation algorithm in step 300 which constitutes entry into the second operating mode. The substituate pump is stopped if the treatment is hemodiafiltration or hemofiltration, in step 320. Otherwise, if it is a hemodialysis treatment, this step is skipped. The ultrafiltration pump is stopped in step 330. The transmembrane and venous pressure limits can be widened in step 340. During a typical treatment using an extracorporeal blood treatment device, transmembrane pressure and venous pressure are monitored to detect malfunctions. In anticipation of the dialysate outlet valve being closed for a duration of time, the TMP limits are temporarily widened to the machine hard limits to prevent the detection of a false malfunction. A step involving adapting dialysate and blood flow rates, if applicable, can be provided as depicted at step 345. Resultant of the cessation of the ultrafiltration pump in step 330 and the optional adaptation of the dialysate and blood flow rates in step 345, the venous pressure limits are temporarily widened to the machine hard limits in step 340 to prevent the detection of a false malfunction.

When a balancing chamber is part of the device, monitoring for the initiation of a new balancing chamber cycle is performed, in step 350. Balancing chambers cycle between two states, where in a first state the fresh side of the balancing chamber is filled emptying the spent side of the balancing chamber, and a second state where the spent side of the balancing chamber is filled emptying the fresh side of the balancing chamber.

If a balancing chamber is present but a balancing chamber cycle is not initiated, the process can be prevented from moving to the next step until the balancing chamber cycle is initiated. Step 350 is skipped if no balancing chamber is present. Then, an instigation of a volume introduction through the closing of the dialysate outlet valve and disabling of the checking of flow errors and the need for a pressure hold test (PHT) is achieved, in step 360.

The closing of the dialysate outlet valve is performed for a first fraction of the balancing chamber cycle, if a balancing chamber is present, and then the dialysate outlet valve would reopen to allow for the balancing chamber cycle to complete. Alternatively, the closing of the dialysate outlet valve would be performed for the duration of step 360 if a balancing chamber is not present. Then, a check is made to determine whether the balancing cycle is complete, in step 370. The process should not move to the next step unless the balancing cycle is complete and is ready to move from a first state to a second state or a second state to a first state. One exception would be the unforeseen event of the venous pressure exceeding the machine hard limit during the second operating mode resultant of the dialysate outlet valve being stuck closed, in which case the dialyzer would be immediately isolated through closure of the dialysate inlet valve to ensure patient safety. Once the balancing cycle is complete, the process instigates recovery by restoring the ultrafiltration rate, restoring the dialysate flow, blood flow, and substitution fluid flow rates, as applicable, and restoring Flow Error/PHT checking after two balancing chamber cycles, in step 380. Completion of step 380 constitutes the completion of the second operating mode and re-entry into the first operating mode.

Upon re-entry into the first operating mode, transmembrane pressure and venous pressure limits are restored and the fluid volume introduced to the patient resultant of the backflush is recovered by increasing ultrafiltration for about 5 to 10 minutes in step 390. Then, the ultrafiltration coefficient is recalculated by triggering the ultrafiltration coefficient/PHT if the ultrafiltration calculation is available, in step 400.

It should be assumed that entry from the first operating mode to the second operating mode occurs when the system is in an alarm-free state, and that the second operating mode would only be entered if prior to entry the dialysate conductivity, dialysate temperature, arterial pressure, venous pressure, and transmembrane pressure were in their respective acceptable ranges. When values for the arterial pressure, venous pressure, and/or transmembrane pressure are close to their respective upper or lower alarm limits, the blood flow rate, dialysate flow rate, or combination thereof can be adjusted during the second operating mode to minimize changes to arterial pressure, venous pressure, and/or transmembrane pressure.

It should further be assumed that if the second operating mode is entered when the machine is priming and a patient is not connected, the base volume to be delivered into the blood chamber of the dialyzer during second operating mode can be delivered at an upper range of duration as described herein. The time interval before a backflush during priming would not be based on equations I-IV, and entry into the secondary operating mode during priming can occur at the start of priming, the end of priming, at some point during priming, or during a combination thereof.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, a preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An extracorporeal blood treatment device comprising:
   a dialyzer comprising a blood chamber, a dialysate chamber, a dialysate inlet, a dialysate outlet, and a semipermeable membrane, the blood chamber and the dialysate chamber being divided from one another by the semipermeable membrane;
   a dialyzer feed line that leads to the dialysate inlet and is configured to supply dialysate to the dialysate chamber;
   a dialyzer discharge line that leads away from the dialysate outlet and is configured to carry dialysate away from the dialysate chamber;
   a dialysate pump configured to pump dialysate through the dialyzer feed line to the dialysate chamber and from the dialysate chamber out through the dialyzer discharge line;
   a dialysate outlet valve;
   a blood pump configured to pump blood through the dialyzer to the blood chamber;
   a processor and a sensor in communication with the processor and configured to generate sensor data; and
   a balancing device comprising a balancing chamber, a balancing feed line that leads to the balancing chamber and is configured to supply dialysate from a dialysate source into the balancing chamber, a balancing discharge line that leads away from the balancing chamber and is configured to carry dialysate away from the balancing chamber into a drain, wherein
   the dialyzer feed line runs from the balancing chamber and is configured to supply dialysate from the balancing chamber to the dialysate chamber, and the dialyzer discharge line leads to the balancing chamber and is configured to supply dialysate from the dialysate chamber into the balancing chamber,
   the dialysate pump, the blood pump, or both, are configured to operate in a first operating mode of the extracorporeal blood treatment device and a second operating mode of the extracorporeal blood treatment device, the first operating mode operates in a configuration wherein the dialysate outlet valve is open such that dialysate flows through the dialyzer feed line, through the dialysate chamber, and into and through the dialyzer discharge line, the second operating mode operates in a configuration wherein the dialysate outlet valve is closed for a duration of time, dialysate is prevented from flowing through the dialyzer discharge line, and a volume of dialysate passes from the dialysate chamber through the semipermeable membrane and into the blood chamber, the processor is configured to process the sensor data and to switch the extracorporeal blood treatment device to the second operating mode from the first operating mode, for a time frame, based on the sensor data processed, the processor is configured to run an initial first operating mode phase for a primary operating time frame, the initial first operating mode phase starting at a beginning of treatment, the processor is configured to switch the extracorporeal blood treatment device from first operating mode to the second operating mode once the operating time frame expires, and the processor is programmed to switch from the first operating mode to a second operating mode upon the expiration of a time interval calculated according to Equation I:

$$T_i = T_B \cdot R_n \cdot Q_s \cdot Q_{uf} \cdot Q_b \cdot X_d \cdot P_v \cdot P_{tm}$$ Equation I wherein $T_i$ is the time interval before a backflush, $T_B$ is the base time, $R_n$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, and $P_{tm}$ is the cm based on the transmembrane pressure.

2. The extracorporeal blood treatment device of claim 1, wherein each of the dialysate pump and blood pump is configured to operate at a respective first operating speed and at a respective second operating speed, and the dialysate pump and blood pump are configured to run at their respective first operating speeds during the first operating mode and at their respective second operating speeds during the second operating mode.

3. The extracorporeal blood treatment device of claim 1, further comprising an ultrafiltrate pump configured to be switched between an operating state and a non-operating state, wherein, in the operating state, the ultrafiltrate pump pulls liquid from the blood chamber, through the semipermeable membrane, into the dialysate chamber, and away from the dialysate chamber, and the ultrafiltrate pump is switched to the non-operating state in the second operating mode.

4. The extracorporeal blood treatment device of claim 1, wherein the processor is configured to run an initial first operating mode phase for a primary operating time frame, the initial first operating mode phase starting at a beginning of priming, and the processor is configured to switch the extracorporeal blood treatment device from first operating mode to the second operating mode once the operating time frame expires.

5. The extracorporeal blood treatment device of claim 1, wherein the processor is configured to process the sensor data and to switch the extracorporeal blood treatment device to the second operating mode from the first operating mode, for a time frame, based on the sensor data processed, the processor is configured to run an initial second operating mode phase for a primary operating time frame, the processor is configured to switch the extracorporeal blood treatment device from second operating mode to the first operating mode once the primary operating time frame expires, and the processor is configured to modify the primary operating time frame based on at least one device setting variable, at least one device output variable, or both.

6. The extracorporeal blood treatment device of claim 1, wherein the processor is configured to alternate the extracorporeal blood treatment device between the first operating mode and the second operating mode in a series of a plurality of operating modes, and at a frequency, over a course of a treatment, each of the plurality of operating modes comprises a respective operating time frame, and the processor is configured to modify at least one of the frequency and each of the respective operating time frames, based on at least one device setting variable, at least one device output variable, or both.

7. The extracorporeal blood treatment device of claim 1, further comprising an extracorporeal blood circuit in fluid communication with the blood chamber, the extracorporeal blood circuit comprising the blood pump, wherein the blood pump is controlled by the processor and the processor is configured to reduce a pump speed of the blood pump during the second operating mode as compared to during the first operating mode.

8. The extracorporeal blood treatment device of claim 1, wherein the volume of dialysate that passes from the dialysate chamber through the semipermeable membrane and into the blood chamber is from 3 ml to 20 ml.

9. An extracorporeal blood treatment device comprising:

a dialyzer comprising a blood chamber, a dialysate chamber, a dialysate inlet, a dialysate outlet, and a semipermeable membrane, the blood chamber and the dialysate chamber being divided from one another by the semipermeable membrane;

a dialyzer feed line that leads to the dialysate inlet and is configured to supply dialysate to the dialysate chamber;

a dialyzer discharge line that leads away from the dialysate outlet and is configured to carry dialysate away from the dialysate chamber;

a dialysate pump configured to pump dialysate through the dialyzer feed line to the dialysate chamber and from the dialysate chamber out through the dialyzer discharge line;

a dialysate outlet valve; and a processor and a sensor in communication with the processor and configured to generate sensor data, wherein the processor is configured to process the sensor data and to switch the extracorporeal blood treatment device to the second operating mode from the first operating mode, for a time frame, based on the sensor data processed, wherein the dialysate pump is configured to operate in a first operating mode of the extracorporeal blood treatment device and a second operating mode of the extracorporeal blood treatment device, the first operating mode operates in a configuration wherein the dialysate outlet valve is open such that dialysate flows through the dialyzer feed line, through the dialysate chamber, and into and through the dialyzer discharge line, the second operating mode operates in a configuration wherein the dialysate outlet valve is closed for a duration of time, dialysate is prevented from flowing through the dialyzer discharge line, and a volume of dialysate passes from the dialysate chamber through the semipermeable membrane and into the blood chamber, the second operating mode is operated continuously for a time frame of no more than 30 seconds, the volume of dialysate that passes from the dialysate chamber to the blood chamber through the semipermeable membrane during the time frame is from 3 ml to 20 ml, and the processor is programmed to switch from the first operating mode to a second operating mode upon the expiration of a time interval calculated according to Equation I:

$$T_i = T_B \cdot R_n \cdot Q_s \cdot Q_{uf} \cdot Q_b \cdot X_d \cdot P_v \cdot P_{tm}$$ Equation I wherein $T_i$ is the time interval before a backflush, $T_B$ is the base time, $R_n$ is the run number coefficient of modification (cm), $Q_s$ is the cm based on the substitution fluid rate and whether the substitution fluid is introduced to the blood before the dialyzer or after the dialyzer, $Q_{uf}$ is the cm based on the UF rate, $Q_b$ is the cm based on the blood flow rate, $X_d$ is the cm based on the type of dialyzer, $P_v$ is the cm based on venous pressure, and $P_{tm}$ is the cm based on the transmembrane pressure.

10. The extracorporeal blood treatment device of claim 9, wherein the dialysate pump is configured to operate at a first operating speed and at a second operating speed, and the dialysate pump is configured to run at the first operating speed during the first operating mode and at the second operating speed during the second operating mode.

11. The extracorporeal blood treatment device of claim 9, further comprising an ultrafiltrate pump configured to be switched between an operating state and a non-operating state, wherein, in the operating state, the ultrafiltrate pump pulls liquid from the blood chamber, through the semipermeable membrane, into the dialysate chamber, and away from the dialysate chamber, and the ultrafiltrate pump is switched to the non-operating state in the second operating mode.

12. The extracorporeal blood treatment device of claim 9, wherein the processor is configured to run an initial first operating mode phase for a primary operating time frame, the initial first operating mode phase starting at a beginning of priming, and the processor is configured to switch the extracorporeal blood treatment device from first operating mode to the second operating mode once the operating time frame expires.

13. The extracorporeal blood treatment device of claim 9, wherein the processor is configured to process the sensor data and to switch the extracorporeal blood treatment device to the second operating mode from the first operating mode, for a time frame, based on the sensor data processed, the processor is configured to run an initial second operating mode phase for a primary operating time frame, the processor is configured to switch the extracorporeal blood treatment device from second operating mode to the first operating mode once the primary operating time frame expires, and the processor is configured to modify the primary operating time frame based on at least one device setting variable, at least one device output variable, or both.

14. The extracorporeal blood treatment device of claim 9, wherein the processor is configured to alternate the extracorporeal blood treatment device between the first operating mode and the second operating mode in a series of a plurality of operating modes, and at a frequency, over a course of a treatment, each of the plurality of operating modes comprises a respective operating time frame, and the processor is configured to modify at least one of the frequency and each of the respective operating time frames, based on at least one device setting variable, at least one device output variable, or both.

15. The extracorporeal blood treatment device of claim 9, further comprising an extracorporeal blood circuit in fluid communication with the blood chamber, the extracorporeal blood circuit comprising a blood pump, wherein the blood pump is controlled by the processor and the processor is configured to reduce a pump speed of the blood pump during the second operating mode as compared to during the first operating mode.

* * * * *